(12) United States Patent
Nibbering et al.

(10) Patent No.: US 9,562,085 B2
(45) Date of Patent: Feb. 7, 2017

(54) ANTIMICROBIAL PEPTIDE

(71) Applicant: Academisch Ziekenhuis Leiden H.O.D.N. LUMC, Leiden (NL)

(72) Inventors: Petrus Hendricus Nibbering, Leiden (NL); Pieter Hiemstra, Leiden (NL); Jan Wouter Drijfhout, Leiden (NL)

(73) Assignee: Academisch Ziekenhuis Leiden H.O.D.N. LUMC, Leiden (NL)

( * ) Notice: Subject to any disclaimer, the term of this patent is extended or adjusted under 35 U.S.C. 154(b) by 0 days.

(21) Appl. No.: 14/890,415

(22) PCT Filed: May 9, 2014

(86) PCT No.: PCT/NL2014/050295
§ 371 (c)(1),
(2) Date: Nov. 10, 2015

(87) PCT Pub. No.: WO2014/182172
PCT Pub. Date: Nov. 13, 2014

(65) Prior Publication Data
US 2016/0075749 A1    Mar. 17, 2016

(30) Foreign Application Priority Data
May 10, 2013 (EP) .................................. 13167240

(51) Int. Cl.
| C07K 14/00 | (2006.01) |
| C07K 14/47 | (2006.01) |
| A61K 38/00 | (2006.01) |
| A61K 45/06 | (2006.01) |
| A61L 27/54 | (2006.01) |

(52) U.S. Cl.
CPC .......... *C07K 14/4723* (2013.01); *A61K 45/06* (2013.01); *A61L 27/54* (2013.01); *A61K 38/00* (2013.01); *A61L 2202/21* (2013.01); *A61L 2202/24* (2013.01); *A61L 2420/04* (2013.01); *A61L 2420/06* (2013.01)

(58) Field of Classification Search
CPC ..... A61K 38/00; A61K 45/06; A61L 2202/21; A61L 2202/24; A61L 2420/04; A61L 2420/06; A61L 27/54; C07K 14/4723; C07K 14/00

USPC ............................ 514/2.3, 2.4; 530/325, 326
See application file for complete search history.

(56) References Cited

U.S. PATENT DOCUMENTS

| 5,646,014 | A | 7/1997 | Hara |
| 5,717,064 | A | 2/1998 | Julian et al. |
| 5,912,230 | A | 6/1999 | Oppenheim et al. |
| 6,495,516 | B1 | 12/2002 | Little, II |
| 6,503,881 | B2 | 1/2003 | Krieger et al. |
| 7,803,756 | B2 * | 9/2010 | Grote ..................... A61K 38/17 514/1.4 |
| 2008/0249022 | A1 | 10/2008 | Grote et al. |
| 2011/0053835 | A1 | 3/2011 | Grote et al. |

FOREIGN PATENT DOCUMENTS

| CN | 101081864 | 12/2007 |
| EP | 2221061 | 8/2010 |
| WO | 0181578 | 11/2001 |
| WO | 2004016653 | 2/2004 |
| WO | 2005040192 | 5/2005 |
| WO | 2006011792 | 2/2006 |
| WO | 2014182172 | 11/2014 |

OTHER PUBLICATIONS

PCT International Search Report and Written Opinion, PCT/EP2014050295 dated Sep. 4, 2014.
E M Haisma et al., The LL-37 Derived Peptides OP-145 and PX are Highly Effective Against Methicillin-resistant *Staphylococcus aureus* and *Pseudomonas Aeruginosa* on Organotypic Skin Cultures, Nederlands Tijdschrift Voor Dermatologie En Venereologie, Jan. 1, 2013, p. 43, vol. 23, No. 1.
Marja J Nell et al., Development of novel LL-37 derived antimicrobial peptides with LPS and LTA neutralizing and antimicrobial activities for therapeutic application, Peptides, Apr. 1, 2006, pp. 649-660, vol. 27, No. 4, Elsevier.

* cited by examiner

Primary Examiner — Julie Ha
(74) Attorney, Agent, or Firm — TraskBritt, P.C.

(57) ABSTRACT

The disclosure relates to antimicrobial peptides, pharmaceutical compositions comprising the peptides and to uses thereof for treatment or prevention of microbial, bacterial, fungal, viral and parasitic infection.

13 Claims, 7 Drawing Sheets

| Peptide | IC90 (uM) | | IC99 (uM) | | IC99.9 (uM) | |
|---|---|---|---|---|---|---|
| P60.4Ac | 0.75 ± | 0.29 | 1.13 ± | 0.34 | 1.51 ± | 0.40 |
| P2 | 0.51 ± | 0.02 | 0.76 ± | 0.00 | 1.02 ± | 0.02 |
| P3 | 0.50 ± | 0.10 | 0.97 ± | 0.10 | 1.44 ± | 0.29 |
| P4 | 0.79 ± | 0.14 | 1.07 ± | 0.10 | 1.35 ± | 0.06 |
| P5 | 0.58 ± | 0.22 | 0.93 ± | 0.21 | 1.28 ± | 0.20 |
| P6 | 0.41 ± | 0.29 | 0.69 ± | 0.46 | 0.97 ± | 0.63 |
| P9 | 2.29 ± | 1.06 | 4.32 ± | 1.72 | 6.35 ± | 2.46 |
| P10 | 0.10 ± | 0.04 | 0.34 ± | 0.04 | 0.59 ± | 0.08 |
| P11 | 1.11 ± | 0.68 | 1.75 ± | 1.21 | 2.39 ± | 1.74 |
| P12 | 0.54 ± | 0.03 | 0.84 ± | 0.11 | 1.14 ± | 0.20 |
| P13 | 0.95 ± | 0.21 | 1.77 ± | 0.34 | 2.59 ± | 0.54 |
| P14 | 0.62 ± | 0.44 | 1.39 ± | 0.89 | 2.15 ± | 1.34 |
| P15 | 1.14 | | 1.85 | | 2.56 | |
| P16 | 2.40 ± | 0.51 | 5.23 ± | 0.65 | 8.07 ± | 0.79 |
| P17 | 2.29 ± | 1.25 | 4.67 ± | 1.92 | 7.05 ± | 2.60 |
| P19 | 1.94 ± | 0.01 | 3.32 ± | 0.03 | 4.70 ± | 0.06 |

FIG. 2B

SEQUENCE LISTING

<160> NUMBER OF SEQ ID NOS: 113

<210> SEQ ID NO 1
<211> LENGTH: 24
<212> TYPE: PRT
<213> ORGANISM: Artificial Sequence
<220> FEATURE:
<223> OTHER INFORMATION: antimicrobial peptide

<400> SEQUENCE: 1

Leu Ala Arg Glu Tyr Lys Lys Ile Val Glu Lys Leu Lys Arg Trp Leu
1               5                   10                  15

Arg Gln Val Leu Arg Thr Leu Arg
            20

<210> SEQ ID NO 2
<211> LENGTH: 16
<212> TYPE: PRT
<213> ORGANISM: Artificial Sequence
<220> FEATURE:
<223> OTHER INFORMATION: variant AMP

<400> SEQUENCE: 2

Tyr Lys Lys Ile Val Glu Lys Leu Lys Arg Trp Leu Arg Gln Val Leu
1               5                   10                  15

<210> SEQ ID NO 3
<211> LENGTH: 24
<212> TYPE: PRT
<213> ORGANISM: Artificial Sequence
<220> FEATURE:
<223> OTHER INFORMATION: variant AMP

<400> SEQUENCE: 3

Leu Ala Arg Glu Tyr Lys Lys Ile Val Glu Lys Leu Lys Arg Trp Leu
1               5                   10                  15

Arg Gln Val Leu Arg Thr Leu Arg
            20

<210> SEQ ID NO 4
<211> LENGTH: 24
<212> TYPE: PRT
<213> ORGANISM: Artificial Sequence
<220> FEATURE:
<223> OTHER INFORMATION: variant AMP -continued

<400> SEQUENCE: 4

Ile Ala Arg Glu Tyr Lys Lys Ile Val Glu Lys Leu Lys Arg Trp Leu
1               5                   10                  15

Arg Gln Val Leu Arg Thr Leu Arg
            20

<210> SEQ ID NO 5
<211> LENGTH: 24
<212> TYPE: PRT
<213> ORGANISM: Artificial Sequence
<220> FEATURE:
<223> OTHER INFORMATION: variant AMP

<400> SEQUENCE: 5

Val Ala Arg Glu Tyr Lys Lys Ile Val Glu Lys Leu Lys Arg Trp Leu
1               5                   10                  15

Arg Gln Val Leu Arg Thr Leu Arg
            20

<210> SEQ ID NO 6
<211> LENGTH: 24
<212> TYPE: PRT
<213> ORGANISM: Artificial Sequence
<220> FEATURE:
<223> OTHER INFORMATION: variant AMP

<400> SEQUENCE: 6

Ala Ala Arg Glu Tyr Lys Lys Ile Val Glu Lys Leu Lys Arg Trp Leu
1               5                   10                  15

Arg Gln Val Leu Arg Thr Leu Arg
            20

<210> SEQ ID NO 7
<211> LENGTH: 24
<212> TYPE: PRT
<213> ORGANISM: Artificial Sequence
<220> FEATURE:
<223> OTHER INFORMATION: variant AMP

<400> SEQUENCE: 7

Leu Leu Arg Glu Tyr Lys Lys Ile Val Glu Lys Leu Lys Arg Trp Leu
1               5                   10                  15

Arg Gln Val Leu Arg Thr Leu Arg
            20

<210> SEQ ID NO 8
<211> LENGTH: 24
<212> TYPE: PRT
<213> ORGANISM: Artificial Sequence
<220> FEATURE:
<223> OTHER INFORMATION: variant AMP

<400> SEQUENCE: 8

Leu Val Arg Glu Tyr Lys Lys Ile Val Glu Lys Leu Lys Arg Trp Leu
1               5                   10                  15

Arg Gln Val Leu Arg Thr Leu Arg
            20

<210> SEQ ID NO 9
<211> LENGTH: 24
<212> TYPE: PRT
<213> ORGANISM: Artificial Sequence
<220> FEATURE:

<223> OTHER INFORMATION: variant AMP

<400> SEQUENCE: 9

Leu Gln Arg Glu Tyr Lys Lys Ile Val Glu Lys Leu Lys Arg Trp Leu
1               5                   10                  15

Arg Gln Val Leu Arg Thr Leu Arg
            20

<210> SEQ ID NO 10
<211> LENGTH: 24
<212> TYPE: PRT
<213> ORGANISM: Artificial Sequence
<220> FEATURE:
<223> OTHER INFORMATION: variant AMP

<400> SEQUENCE: 10

Leu Ala Lys Glu Tyr Lys Lys Ile Val Glu Lys Leu Lys Arg Trp Leu
1               5                   10                  15

Arg Gln Val Leu Arg Thr Leu Arg
            20

<210> SEQ ID NO 11
<211> LENGTH: 24
<212> TYPE: PRT
<213> ORGANISM: Artificial Sequence
<220> FEATURE:
<223> OTHER INFORMATION: variant AMP

<400> SEQUENCE: 11

Leu Ala His Glu Tyr Lys Lys Ile Val Glu Lys Leu Lys Arg Trp Leu
1               5                   10                  15

Arg Gln Val Leu Arg Thr Leu Arg
            20

<210> SEQ ID NO 12
<211> LENGTH: 24
<212> TYPE: PRT
<213> ORGANISM: Artificial Sequence
<220> FEATURE:
<223> OTHER INFORMATION: variant AMP

<400> SEQUENCE: 12

Leu Ala Arg Gln Tyr Lys Lys Ile Val Glu Lys Leu Lys Arg Trp Leu
1               5                   10                  15

Arg Gln Val Leu Arg Thr Leu Arg
            20

<210> SEQ ID NO 13
<211> LENGTH: 24
<212> TYPE: PRT
<213> ORGANISM: Artificial Sequence
<220> FEATURE:
<223> OTHER INFORMATION: variant AMP

<400> SEQUENCE: 13

Leu Ala Arg Glu Phe Lys Lys Ile Val Glu Lys Leu Lys Arg Trp Leu
1               5                   10                  15

Arg Gln Val Leu Arg Thr Leu Arg
            20

<210> SEQ ID NO 14
<211> LENGTH: 24
<212> TYPE: PRT
<213> ORGANISM: Artificial Sequence

```
<220> FEATURE:
<223> OTHER INFORMATION: variant AMP

<400> SEQUENCE: 14

Leu Ala Arg Glu Tyr Arg Lys Ile Val Glu Lys Leu Lys Arg Trp Leu
1               5                   10                  15

Arg Gln Val Leu Arg Thr Leu Arg
            20

<210> SEQ ID NO 15
<211> LENGTH: 24
<212> TYPE: PRT
<213> ORGANISM: Artificial Sequence
<220> FEATURE:
<223> OTHER INFORMATION: variant AMP

<400> SEQUENCE: 15

Leu Ala Arg Glu Tyr His Lys Ile Val Glu Lys Leu Lys Arg Trp Leu
1               5                   10                  15

Arg Gln Val Leu Arg Thr Leu Arg
            20

<210> SEQ ID NO 16
<211> LENGTH: 24
<212> TYPE: PRT
<213> ORGANISM: Artificial Sequence
<220> FEATURE:
<223> OTHER INFORMATION: variant AMP

<400> SEQUENCE: 16

Leu Ala Arg Glu Tyr Lys Arg Ile Val Glu Lys Leu Lys Arg Trp Leu
1               5                   10                  15

Arg Gln Val Leu Arg Thr Leu Arg
            20

<210> SEQ ID NO 17
<211> LENGTH: 24
<212> TYPE: PRT
<213> ORGANISM: Artificial Sequence
<220> FEATURE:
<223> OTHER INFORMATION: variant AMP

<400> SEQUENCE: 17

Leu Ala Arg Glu Tyr Lys Lys Ile Val Glu Lys Leu Lys Lys Trp Leu
1               5                   10                  15

Arg Gln Val Leu Arg Thr Leu Arg
            20

<210> SEQ ID NO 18
<211> LENGTH: 24
<212> TYPE: PRT
<213> ORGANISM: Artificial Sequence
<220> FEATURE:
<223> OTHER INFORMATION: variant AMP

<400> SEQUENCE: 18

Leu Ala Arg Glu Tyr Lys Lys Ile Val Glu Lys Leu Lys Arg Phe Leu
1               5                   10                  15

Arg Gln Val Leu Arg Thr Leu Arg
            20

<210> SEQ ID NO 19
<211> LENGTH: 24
<212> TYPE: PRT
```

```
<213> ORGANISM: Artificial Sequence
<220> FEATURE:
<223> OTHER INFORMATION: variant AMP

<400> SEQUENCE: 19

Leu Ala Arg Glu Tyr Lys Lys Ile Val Glu Lys Leu Lys Arg Trp Leu
1               5                   10                  15

His Gln Val Leu Arg Thr Leu Arg
            20

<210> SEQ ID NO 20
<211> LENGTH: 24
<212> TYPE: PRT
<213> ORGANISM: Artificial Sequence
<220> FEATURE:
<223> OTHER INFORMATION: variant AMP

<400> SEQUENCE: 20

Leu Ala Arg Glu Tyr Lys Lys Ile Val Glu Lys Leu Lys Arg Trp Leu
1               5                   10                  15

Arg Asn Val Leu Arg Thr Leu Arg
            20

<210> SEQ ID NO 21
<211> LENGTH: 24
<212> TYPE: PRT
<213> ORGANISM: Artificial Sequence
<220> FEATURE:
<223> OTHER INFORMATION: variant AMP

<400> SEQUENCE: 21

Leu Ala Arg Glu Tyr Lys Lys Ile Val Glu Lys Leu Lys Arg Trp Leu
1               5                   10                  15

Arg Ala Val Leu Arg Thr Leu Arg
            20

<210> SEQ ID NO 22
<211> LENGTH: 24
<212> TYPE: PRT
<213> ORGANISM: Artificial Sequence
<220> FEATURE:
<223> OTHER INFORMATION: variant AMP

<400> SEQUENCE: 22

Leu Ala Arg Glu Tyr Lys Lys Ile Val Glu Lys Leu Lys Arg Trp Leu
1               5                   10                  15

Arg Ser Val Leu Arg Thr Leu Arg
            20

<210> SEQ ID NO 23
<211> LENGTH: 24
<212> TYPE: PRT
<213> ORGANISM: Artificial Sequence
<220> FEATURE:
<223> OTHER INFORMATION: variant AMP

<400> SEQUENCE: 23

Leu Ala Arg Glu Tyr Lys Lys Ile Val Glu Lys Leu Lys Arg Trp Leu
1               5                   10                  15

Arg Thr Val Leu Arg Thr Leu Arg
            20

<210> SEQ ID NO 24
<211> LENGTH: 24
```

```
<212> TYPE: PRT
<213> ORGANISM: Artificial Sequence
<220> FEATURE:
<223> OTHER INFORMATION: variant AMP

<400> SEQUENCE: 24

Leu Ala Arg Glu Tyr Lys Lys Ile Val Glu Lys Leu Lys Arg Trp Leu
1               5                   10                  15

Arg Gln Leu Leu Arg Thr Leu Arg
            20

<210> SEQ ID NO 25
<211> LENGTH: 24
<212> TYPE: PRT
<213> ORGANISM: Artificial Sequence
<220> FEATURE:
<223> OTHER INFORMATION: variant AMP

<400> SEQUENCE: 25

Leu Ala Arg Glu Tyr Lys Lys Ile Val Glu Lys Leu Lys Arg Trp Leu
1               5                   10                  15

Arg Gln Val Ile Arg Thr Leu Arg
            20

<210> SEQ ID NO 26
<211> LENGTH: 24
<212> TYPE: PRT
<213> ORGANISM: Artificial Sequence
<220> FEATURE:
<223> OTHER INFORMATION: variant AMP

<400> SEQUENCE: 26

Leu Ala Arg Glu Tyr Lys Lys Ile Val Glu Lys Leu Lys Arg Trp Leu
1               5                   10                  15

Arg Gln Val Val Arg Thr Leu Arg
            20

<210> SEQ ID NO 27
<211> LENGTH: 24
<212> TYPE: PRT
<213> ORGANISM: Artificial Sequence
<220> FEATURE:
<223> OTHER INFORMATION: variant AMP

<400> SEQUENCE: 27

Leu Ala Arg Glu Tyr Lys Lys Ile Val Glu Lys Leu Lys Arg Trp Leu
1               5                   10                  15

Arg Gln Val Ala Arg Thr Leu Arg
            20

<210> SEQ ID NO 28
<211> LENGTH: 24
<212> TYPE: PRT
<213> ORGANISM: Artificial Sequence
<220> FEATURE:
<223> OTHER INFORMATION: variant AMP

<400> SEQUENCE: 28

Leu Ala Arg Glu Tyr Lys Lys Ile Val Glu Lys Leu Lys Arg Trp Leu
1               5                   10                  15

Arg Gln Val Leu Lys Thr Leu Arg
            20

<210> SEQ ID NO 29
```

<211> LENGTH: 24
<212> TYPE: PRT
<213> ORGANISM: Artificial Sequence
<220> FEATURE:
<223> OTHER INFORMATION: variant AMP

<400> SEQUENCE: 29

Leu Ala Arg Glu Tyr Lys Lys Ile Val Glu Lys Leu Lys Arg Trp Leu
1               5                   10                  15

Arg Gln Val Leu His Thr Leu Arg
            20

<210> SEQ ID NO 30
<211> LENGTH: 24
<212> TYPE: PRT
<213> ORGANISM: Artificial Sequence
<220> FEATURE:
<223> OTHER INFORMATION: variant AMP

<400> SEQUENCE: 30

Leu Ala Arg Glu Tyr Lys Lys Ile Val Glu Lys Leu Lys Arg Trp Leu
1               5                   10                  15

Arg Gln Val Leu Arg Gln Leu Arg
            20

<210> SEQ ID NO 31
<211> LENGTH: 24
<212> TYPE: PRT
<213> ORGANISM: Artificial Sequence
<220> FEATURE:
<223> OTHER INFORMATION: variant AMP

<400> SEQUENCE: 31

Leu Ala Arg Glu Tyr Lys Lys Ile Val Glu Lys Leu Lys Arg Trp Leu
1               5                   10                  15

Arg Gln Val Leu Arg Asn Leu Arg
            20

<210> SEQ ID NO 32
<211> LENGTH: 24
<212> TYPE: PRT
<213> ORGANISM: Artificial Sequence
<220> FEATURE:
<223> OTHER INFORMATION: variant AMP

<400> SEQUENCE: 32

Leu Ala Arg Glu Tyr Lys Lys Ile Val Glu Lys Leu Lys Arg Trp Leu
1               5                   10                  15

Arg Gln Val Leu Arg Ala Leu Arg
            20

<210> SEQ ID NO 33
<211> LENGTH: 24
<212> TYPE: PRT
<213> ORGANISM: Artificial Sequence
<220> FEATURE:
<223> OTHER INFORMATION: variant AMP

<400> SEQUENCE: 33

Leu Ala Arg Glu Tyr Lys Lys Ile Val Glu Lys Leu Lys Arg Trp Leu
1               5                   10                  15

Arg Gln Val Leu Arg Thr Leu His
            20

<210> SEQ ID NO 34
<211> LENGTH: 22
<212> TYPE: PRT
<213> ORGANISM: Artificial Sequence
<220> FEATURE:
<223> OTHER INFORMATION: variant AMP

<400> SEQUENCE: 34

Arg Glu Tyr Lys Lys Ile Val Glu Lys Leu Lys Arg Trp Leu Arg Gln
1               5                   10                  15

Val Leu Arg Thr Leu Arg
            20

<210> SEQ ID NO 35
<211> LENGTH: 22
<212> TYPE: PRT
<213> ORGANISM: Artificial Sequence
<220> FEATURE:
<223> OTHER INFORMATION: variant AMP

<400> SEQUENCE: 35

Leu Ala Arg Glu Tyr Lys Lys Ile Val Glu Lys Leu Lys Arg Trp Leu
1               5                   10                  15

Arg Gln Val Leu Arg Thr
            20

<210> SEQ ID NO 36
<211> LENGTH: 20
<212> TYPE: PRT
<213> ORGANISM: Artificial Sequence
<220> FEATURE:
<223> OTHER INFORMATION: variant AMP

<400> SEQUENCE: 36

Arg Glu Tyr Lys Lys Ile Val Glu Lys Leu Lys Arg Trp Leu Arg Gln
1               5                   10                  15

Val Leu Arg Thr
            20

<210> SEQ ID NO 37
<211> LENGTH: 20
<212> TYPE: PRT
<213> ORGANISM: Artificial Sequence
<220> FEATURE:
<223> OTHER INFORMATION: variant AMP

<400> SEQUENCE: 37

Tyr Lys Lys Ile Val Glu Lys Leu Lys Arg Trp Leu Arg Gln Val Leu
1               5                   10                  15

Arg Thr Leu Arg
            20

<210> SEQ ID NO 38
<211> LENGTH: 20
<212> TYPE: PRT
<213> ORGANISM: Artificial Sequence
<220> FEATURE:
<223> OTHER INFORMATION: variant AMP

<400> SEQUENCE: 38

Leu Ala Arg Glu Tyr Lys Lys Ile Val Glu Lys Leu Lys Arg Trp Leu
1               5                   10                  15

Arg Gln Val Leu
            20

<210> SEQ ID NO 39
<211> LENGTH: 18
<212> TYPE: PRT
<213> ORGANISM: Artificial Sequence
<220> FEATURE:
<223> OTHER INFORMATION: variant AMP

<400> SEQUENCE: 39

```
Glu Tyr Lys Lys Ile Val Glu Lys Leu Lys Arg Trp Leu Arg Gln Val
1               5                   10                  15

Leu Arg
```

<210> SEQ ID NO 40
<211> LENGTH: 16
<212> TYPE: PRT
<213> ORGANISM: Artificial Sequence
<220> FEATURE:
<223> OTHER INFORMATION: variant AMP

<400> SEQUENCE: 40

```
Tyr Lys Lys Ile Val Glu Lys Leu Lys Arg Trp Leu Arg Gln Val Leu
1               5                   10                  15
```

<210> SEQ ID NO 41
<211> LENGTH: 24
<212> TYPE: PRT
<213> ORGANISM: Artificial Sequence
<220> FEATURE:
<223> OTHER INFORMATION: P60.4Ac variant

<400> SEQUENCE: 41

```
Ile Gly Lys Glu Phe Lys Arg Ile Val Glu Arg Ile Lys Arg Phe Leu
1               5                   10                  15

Arg Glu Leu Val Arg Pro Leu Arg
                20
```

<210> SEQ ID NO 42
<211> LENGTH: 24
<212> TYPE: PRT
<213> ORGANISM: Artificial Sequence
<220> FEATURE:
<223> OTHER INFORMATION: P60.4Ac variant

<400> SEQUENCE: 42

```
Ile Ala Lys Glu Phe Lys Arg Ile Val Glu Arg Ile Lys Arg Phe Leu
1               5                   10                  15

Arg Glu Leu Val Arg Pro Leu Arg
                20
```

<210> SEQ ID NO 43
<211> LENGTH: 24
<212> TYPE: PRT
<213> ORGANISM: Artificial Sequence
<220> FEATURE:
<223> OTHER INFORMATION: P60.4Ac variant

<400> SEQUENCE: 43

```
Leu Ala Arg Asp Tyr Lys Arg Leu Val Glu Arg Leu Lys Arg Trp Leu
1               5                   10                  15

Arg Glu Leu Val Arg Pro Leu Lys
                20
```

<210> SEQ ID NO 44
<211> LENGTH: 24

<212> TYPE: PRT
<213> ORGANISM: Artificial Sequence
<220> FEATURE:
<223> OTHER INFORMATION: P60.4Ac variant

<400> SEQUENCE: 44

Ile Ala Lys Glu Phe Lys Arg Ile Leu Glu Arg Ile Lys Arg Phe Ile
1               5                   10                  15

Arg Glu Ile Thr Arg Pro Ile Arg
            20

<210> SEQ ID NO 45
<211> LENGTH: 24
<212> TYPE: PRT
<213> ORGANISM: Artificial Sequence
<220> FEATURE:
<223> OTHER INFORMATION: P60.4Ac variant

<400> SEQUENCE: 45

Thr Ala Lys Glu Tyr Lys Arg Ile Leu Asp Arg Ile Lys Arg Tyr Leu
1               5                   10                  15

Arg Glu Leu Val Arg Ala Ile Lys
            20

<210> SEQ ID NO 46
<211> LENGTH: 24
<212> TYPE: PRT
<213> ORGANISM: Artificial Sequence
<220> FEATURE:
<223> OTHER INFORMATION: P60.4Ac variant

<400> SEQUENCE: 46

Val Ala Lys Asp Tyr Arg Lys Val Val Asp Arg Ile Lys Arg Phe Leu
1               5                   10                  15

Arg Tyr Leu Leu Arg Pro Val Arg
            20

<210> SEQ ID NO 47
<211> LENGTH: 24
<212> TYPE: PRT
<213> ORGANISM: Artificial Sequence
<220> FEATURE:
<223> OTHER INFORMATION: P60.4Ac variant

<400> SEQUENCE: 47

Leu Ala Lys Asp Tyr Lys Lys Ile Val Glu Arg Leu Arg Lys Trp Leu
1               5                   10                  15

Arg Glu Val Leu Arg Pro Val Lys
            20

<210> SEQ ID NO 48
<211> LENGTH: 24
<212> TYPE: PRT
<213> ORGANISM: Artificial Sequence
<220> FEATURE:
<223> OTHER INFORMATION: P60.4Ac variant

<400> SEQUENCE: 48

Leu Ala Arg Glu Tyr Lys Lys Ile Val Glu Lys Leu Lys Arg Trp Leu
1               5                   10                  15

Arg Gln Val Leu Arg Thr Leu Arg
            20

<210> SEQ ID NO 49

```
<211> LENGTH: 24
<212> TYPE: PRT
<213> ORGANISM: Artificial Sequence
<220> FEATURE:
<223> OTHER INFORMATION: P60.4Ac variant

<400> SEQUENCE: 49

Leu Ala Lys Glu Tyr Arg Lys Ile Phe Asp Arg Leu Lys Lys Trp Leu
1               5                   10                  15

Arg Gln Ile Val Arg Pro Ser Lys
            20

<210> SEQ ID NO 50
<211> LENGTH: 24
<212> TYPE: PRT
<213> ORGANISM: Artificial Sequence
<220> FEATURE:
<223> OTHER INFORMATION: P60.4Ac variant

<400> SEQUENCE: 50

Leu Ala Arg Glu Tyr Lys Arg Ile Phe Glu Arg Leu Arg Lys Trp Leu
1               5                   10                  15

Arg Gln Ile Val Lys Pro Val Arg
            20

<210> SEQ ID NO 51
<211> LENGTH: 24
<212> TYPE: PRT
<213> ORGANISM: Artificial Sequence
<220> FEATURE:
<223> OTHER INFORMATION: P60.4Ac variant

<400> SEQUENCE: 51

Leu Ala Lys Glu Trp Arg Lys Ile Val Asp Arg Leu Lys Arg Trp Leu
1               5                   10                  15

Arg Asp Ile Leu Lys Ala Thr Lys
            20

<210> SEQ ID NO 52
<211> LENGTH: 24
<212> TYPE: PRT
<213> ORGANISM: Artificial Sequence
<220> FEATURE:
<223> OTHER INFORMATION: P60.4Ac variant

<400> SEQUENCE: 52

Val Ala Arg Glu Trp Lys Arg Ile Leu Glu Lys Ile Lys Arg Trp Leu
1               5                   10                  15

Arg Asp Ile Leu Lys Ala Leu Arg
            20

<210> SEQ ID NO 53
<211> LENGTH: 24
<212> TYPE: PRT
<213> ORGANISM: Artificial Sequence
<220> FEATURE:
<223> OTHER INFORMATION: P60.4Ac variant

<400> SEQUENCE: 53

Val Ala Lys Glu Trp Arg Lys Ile Val Asp Arg Ile Lys Arg Tyr Leu
1               5                   10                  15

Arg Asp Ile Ser Lys Ala Thr Lys
            20
```

```
<210> SEQ ID NO 54
<211> LENGTH: 24
<212> TYPE: PRT
<213> ORGANISM: Artificial Sequence
<220> FEATURE:
<223> OTHER INFORMATION: P60.4Ac variant

<400> SEQUENCE: 54

Thr Ala Arg Glu Trp Lys Arg Ile Leu Glu Lys Ile Arg Lys Tyr Leu
1               5                   10                  15

Arg Asp Val Ser Arg Val Thr Arg
            20

<210> SEQ ID NO 55
<211> LENGTH: 24
<212> TYPE: PRT
<213> ORGANISM: Artificial Sequence
<220> FEATURE:
<223> OTHER INFORMATION: P60.4Ac variant

<400> SEQUENCE: 55

Val Ala Lys Asp Trp Lys Arg Ile Val Asp Lys Val Arg Arg Tyr Leu
1               5                   10                  15

Arg Glu Val Thr Lys Ile Leu Lys
            20

<210> SEQ ID NO 56
<211> LENGTH: 24
<212> TYPE: PRT
<213> ORGANISM: Artificial Sequence
<220> FEATURE:
<223> OTHER INFORMATION: P60.4Ac variant

<400> SEQUENCE: 56

Thr Ala Lys Asp Tyr Arg Lys Ile Phe Glu Lys Ile Lys Lys Tyr Leu
1               5                   10                  15

Lys Asp Leu Thr Arg Ile Leu Lys
            20

<210> SEQ ID NO 57
<211> LENGTH: 24
<212> TYPE: PRT
<213> ORGANISM: Artificial Sequence
<220> FEATURE:
<223> OTHER INFORMATION: proline variant of P10
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 57

Leu Ala Arg Glu Tyr Lys Pro Ile Val Glu Lys Leu Lys Arg Trp Pro
1               5                   10                  15

Arg Gln Val Leu Arg Thr Leu Arg
            20

<210> SEQ ID NO 58
<211> LENGTH: 24
<212> TYPE: PRT
<213> ORGANISM: Artificial Sequence
<220> FEATURE:
<223> OTHER INFORMATION: proline variant of P10
<220> FEATURE:
```

```
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 58

Leu Ala Arg Glu Tyr Pro Lys Ile Val Glu Lys Leu Lys Arg Trp Leu
1               5                   10                  15

Arg Pro Val Leu Arg Thr Leu Arg
            20

<210> SEQ ID NO 59
<211> LENGTH: 24
<212> TYPE: PRT
<213> ORGANISM: Artificial Sequence
<220> FEATURE:
<223> OTHER INFORMATION: proline variant of P10
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 59

Leu Ala Arg Glu Tyr Lys Lys Ile Val Pro Lys Leu Lys Arg Trp Leu
1               5                   10                  15

Arg Gln Val Pro Arg Thr Leu Arg
            20

<210> SEQ ID NO 60
<211> LENGTH: 24
<212> TYPE: PRT
<213> ORGANISM: Artificial Sequence
<220> FEATURE:
<223> OTHER INFORMATION: proline variant of P10
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 60

Leu Ala Arg Glu Tyr Lys Lys Pro Val Glu Lys Leu Lys Arg Trp Leu
1               5                   10                  15

Pro Gln Val Leu Arg Thr Leu Arg
            20

<210> SEQ ID NO 61
<211> LENGTH: 24
<212> TYPE: PRT
<213> ORGANISM: Artificial Sequence
<220> FEATURE:
<223> OTHER INFORMATION: p10variant
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION
```

<400> SEQUENCE: 61

Leu Ala Arg Glu Tyr Lys Lys Ile Val Glu Lys Leu Lys Arg Trp Leu
1               5                   10                  15

Arg Gln Val Leu Arg Thr Leu Arg
            20

<210> SEQ ID NO 62
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 62

Ile Ala Arg Glu Tyr Lys Lys Ile Val Glu Lys Leu Lys Arg Trp Leu
1               5                   10                  15

Arg Gln Val Leu Arg Thr Leu Arg
            20

<210> SEQ ID NO 63
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 63

Val Ala Arg Glu Tyr Lys Lys Ile Val Glu Lys Leu Lys Arg Trp Leu
1               5                   10                  15

Arg Gln Val Leu Arg Thr Leu Arg
            20

<210> SEQ ID NO 64
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 64

Leu Leu Arg Glu Tyr Lys Lys Ile Val Glu Lys Leu Lys Arg Trp Leu
1               5                   10                  15

Arg Gln Val Leu Arg Thr Leu Arg

-continued

20

<210> SEQ ID NO 65
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 65

Leu Val Arg Glu Tyr Lys Lys Ile Val Glu Lys Leu Lys Arg Trp Leu
1               5                   10                  15

Arg Gln Val Leu Arg Thr Leu Arg
            20

<210> SEQ ID NO 66
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 66

Ala Ala Arg Glu Tyr Lys Lys Ile Val Glu Lys Leu Lys Arg Trp Leu
1               5                   10                  15

Arg Gln Val Leu Arg Thr Leu Arg
            20

<210> SEQ ID NO 67
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 67

Leu Gln Arg Glu Tyr Lys Lys Ile Val Glu Lys Leu Lys Arg Trp Leu
1               5                   10                  15

Arg Gln Val Leu Arg Thr Leu Arg
            20

<210> SEQ ID NO 68
<211> LENGTH: 24
<212> TYPE: PRT
<213> ORGANISM: Artificial Sequence

```
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 68

Leu Ala Lys Glu Tyr Lys Lys Ile Val Glu Lys Leu Lys Arg Trp Leu
1               5                   10                  15

Arg Gln Val Leu Arg Thr Leu Arg
            20

<210> SEQ ID NO 69
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 69

Leu Ala His Glu Tyr Lys Lys Ile Val Glu Lys Leu Lys Arg Trp Leu
1               5                   10                  15

Arg Gln Val Leu Arg Thr Leu Arg
            20

<210> SEQ ID NO 70
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 70

Leu Ala Arg Gln Tyr Lys Lys Ile Val Glu Lys Leu Lys Arg Trp Leu
1               5                   10                  15

Arg Gln Val Leu Arg Thr Leu Arg
            20

<210> SEQ ID NO 71
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
```

```
<221> NAME/KEY: MOD_RES
<222> LOCATION: (24)..(24)
<223> OTHER INFORMATION: AMIDATION

<400> SEQUENCE: 71

Leu Ala Arg Glu Phe Lys Lys Ile Val Glu Lys Leu Lys Arg Trp Leu
1               5                   10                  15

Arg Gln Val Leu Arg Thr Leu Arg
            20

<210> SEQ ID NO 72
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 72

Leu Ala Arg Glu Tyr Arg Lys Ile Val Glu Lys Leu Lys Arg Trp Leu
1               5                   10                  15

Arg Gln Val Leu Arg Thr Leu Arg
            20

<210> SEQ ID NO 73
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 73

Leu Ala Arg Glu Tyr His Lys Ile Val Glu Lys Leu Lys Arg Trp Leu
1               5                   10                  15

Arg Gln Val Leu Arg Thr Leu Arg
            20

<210> SEQ ID NO 74
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 74

Leu Ala Arg Glu Tyr Lys Arg Ile Val Glu Lys Leu Lys Arg Trp Leu
```

```
                1               5                   10                  15
Arg Gln Val Leu Arg Thr Leu Arg
            20

<210> SEQ ID NO 75
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 75

Leu Ala Arg Glu Tyr Lys His Ile Val Glu Lys Leu Lys Arg Trp Leu
1               5                   10                  15

Arg Gln Val Leu Arg Thr Leu Arg
            20

<210> SEQ ID NO 76
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 76

Leu Ala Arg Glu Tyr Lys Lys Ile Val Glu Arg Leu Lys Arg Trp Leu
1               5                   10                  15

Arg Gln Val Leu Arg Thr Leu Arg
            20

<210> SEQ ID NO 77
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 77

Leu Ala Arg Glu Tyr Lys Lys Ile Val Glu His Leu Lys Arg Trp Leu
1               5                   10                  15

Arg Gln Val Leu Arg Thr Leu Arg
            20

<210> SEQ ID NO 78
```

```
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 78

Leu Ala Arg Glu Tyr Lys Lys Ile Val Glu Lys Ile Lys Arg Trp Leu
1               5                   10                  15

Arg Gln Val Leu Arg Thr Leu Arg
            20

<210> SEQ ID NO 79
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 79

Leu Ala Arg Glu Tyr Lys Lys Ile Val Glu Lys Val Lys Arg Trp Leu
1               5                   10                  15

Arg Gln Val Leu Arg Thr Leu Arg
            20

<210> SEQ ID NO 80
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 80

Leu Ala Arg Glu Tyr Lys Lys Ile Val Glu Lys Ala Lys Arg Trp Leu
1               5                   10                  15

Arg Gln Val Leu Arg Thr Leu Arg
            20

<210> SEQ ID NO 81
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
```

```
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 81

Leu Ala Arg Glu Tyr Lys Lys Ile Val Glu Lys Leu His Arg Trp Leu
1               5                   10                  15

Arg Gln Val Leu Arg Thr Leu Arg
            20

<210> SEQ ID NO 82
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 82

Leu Ala Arg Glu Tyr Lys Lys Ile Val Glu Lys Leu Lys Lys Trp Leu
1               5                   10                  15

Arg Gln Val Leu Arg Thr Leu Arg
            20

<210> SEQ ID NO 83
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 83

Leu Ala Arg Glu Tyr Lys Lys Ile Val Glu Lys Leu Lys His Trp Leu
1               5                   10                  15

Arg Gln Val Leu Arg Thr Leu Arg
            20

<210> SEQ ID NO 84
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION
```

-continued

```
<400> SEQUENCE: 84

Leu Ala Arg Glu Tyr Lys Lys Ile Val Glu Lys Leu Lys Arg Phe Leu
1               5                   10                  15

Arg Gln Val Leu Arg Thr Leu Arg
            20

<210> SEQ ID NO 85
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 85

Leu Ala Arg Glu Tyr Lys Lys Ile Val Glu Lys Leu Lys Arg Trp Leu
1               5                   10                  15

His Gln Val Leu Arg Thr Leu Arg
            20

<210> SEQ ID NO 86
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 86

Leu Ala Arg Glu Tyr Lys Lys Ile Val Glu Lys Leu Lys Arg Trp Leu
1               5                   10                  15

Arg Asn Val Leu Arg Thr Leu Arg
            20

<210> SEQ ID NO 87
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 87

Leu Ala Arg Glu Tyr Lys Lys Ile Val Glu Lys Leu Lys Arg Trp Leu
1               5                   10                  15

Arg Ala Val Leu Arg Thr Leu Arg
            20
```

```
<210> SEQ ID NO 88
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 88

Leu Ala Arg Glu Tyr Lys Lys Ile Val Glu Lys Leu Lys Arg Trp Leu
1               5                   10                  15

Arg Ser Val Leu Arg Thr Leu Arg
            20

<210> SEQ ID NO 89
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 89

Leu Ala Arg Glu Tyr Lys Lys Ile Val Glu Lys Leu Lys Arg Trp Leu
1               5                   10                  15

Arg Thr Val Leu Arg Thr Leu Arg
            20

<210> SEQ ID NO 90
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 90

Leu Ala Arg Glu Tyr Lys Lys Ile Val Glu Lys Leu Lys Arg Trp Leu
1               5                   10                  15

Arg Gln Leu Leu Arg Thr Leu Arg
            20

<210> SEQ ID NO 91
<211> LENGTH: 24
<212> TYPE: PRT
<213> ORGANISM: Artificial Sequence
<220> FEATURE:
```

<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 91

Leu Ala Arg Glu Tyr Lys Lys Ile Val Glu Lys Leu Lys Arg Trp Leu
1               5                   10                  15

Arg Gln Val Ile Arg Thr Leu Arg
            20

<210> SEQ ID NO 92
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 92

Leu Ala Arg Glu Tyr Lys Lys Ile Val Glu Lys Leu Lys Arg Trp Leu
1               5                   10                  15

Arg Gln Val Val Arg Thr Leu Arg
            20

<210> SEQ ID NO 93
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 93

Leu Ala Arg Glu Tyr Lys Lys Ile Val Glu Lys Leu Lys Arg Trp Leu
1               5                   10                  15

Arg Gln Val Ala Arg Thr Leu Arg
            20

<210> SEQ ID NO 94
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES

```
<222> LOCATION: (24)..(24)
<223> OTHER INFORMATION: AMIDATION

<400> SEQUENCE: 94

Leu Ala Arg Glu Tyr Lys Lys Ile Val Glu Lys Leu Lys Arg Trp Leu
1               5                   10                  15
Arg Gln Val Leu Lys Thr Leu Arg
            20

<210> SEQ ID NO 95
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 95

Leu Ala Arg Glu Tyr Lys Lys Ile Val Glu Lys Leu Lys Arg Trp Leu
1               5                   10                  15
Arg Gln Val Leu His Thr Leu Arg
            20

<210> SEQ ID NO 96
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 96

Leu Ala Arg Glu Tyr Lys Lys Ile Val Glu Lys Leu Lys Arg Trp Leu
1               5                   10                  15
Arg Gln Val Leu Arg Gln Leu Arg
            20

<210> SEQ ID NO 97
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 97

Leu Ala Arg Glu Tyr Lys Lys Ile Val Glu Lys Leu Lys Arg Trp Leu
1               5                   10                  15
```

```
Arg Gln Val Leu Arg Asn Leu Arg
            20

<210> SEQ ID NO 98
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 98

Leu Ala Arg Glu Tyr Lys Lys Ile Val Glu Lys Leu Lys Arg Trp Leu
1               5                   10                  15

Arg Gln Val Leu Arg Ala Leu Arg
            20

<210> SEQ ID NO 99
<211> LENGTH: 24
<212> TYPE: PRT
<213> ORGANISM: Artificial Sequence
<220> FEATURE:
<223> OTHER INFORMATION: Acetylated and amidated P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 99

Leu Ala Arg Glu Tyr Lys Lys Ile Val Glu Lys Leu Lys Arg Trp Leu
1               5                   10                  15

Arg Gln Val Leu Arg Thr Leu His
            20

<210> SEQ ID NO 100
<211> LENGTH: 22
<212> TYPE: PRT
<213> ORGANISM: Artificial Sequence
<220> FEATURE:
<223> OTHER INFORMATION: shorth P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (22)..(22)
<223> OTHER INFORMATION: AMIDATION

<400> SEQUENCE: 100

Arg Glu Tyr Lys Lys Ile Val Glu Lys Leu Lys Arg Trp Leu Arg Gln
1               5                   10                  15

Val Leu Arg Thr Leu Arg
            20

<210> SEQ ID NO 101
<211> LENGTH: 22
```

```
<212> TYPE: PRT
<213> ORGANISM: Artificial Sequence
<220> FEATURE:
<223> OTHER INFORMATION: shorth P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (22)..(22)
<223> OTHER INFORMATION: AMIDATION

<400> SEQUENCE: 101

Leu Ala Arg Glu Tyr Lys Lys Ile Val Glu Lys Leu Lys Arg Trp Leu
1               5                   10                  15

Arg Gln Val Leu Arg Thr
            20

<210> SEQ ID NO 102
<211> LENGTH: 20
<212> TYPE: PRT
<213> ORGANISM: Artificial Sequence
<220> FEATURE:
<223> OTHER INFORMATION: shorth P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (20)..(20)
<223> OTHER INFORMATION: AMIDATION

<400> SEQUENCE: 102

Arg Glu Tyr Lys Lys Ile Val Glu Lys Leu Lys Arg Trp Leu Arg Gln
1               5                   10                  15

Val Leu Arg Thr
            20

<210> SEQ ID NO 103
<211> LENGTH: 20
<212> TYPE: PRT
<213> ORGANISM: Artificial Sequence
<220> FEATURE:
<223> OTHER INFORMATION: shorth P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (20)..(20)
<223> OTHER INFORMATION: AMIDATION

<400> SEQUENCE: 103

Tyr Lys Lys Ile Val Glu Lys Leu Lys Arg Trp Leu Arg Gln Val Leu
1               5                   10                  15

Arg Thr Leu Arg
            20

<210> SEQ ID NO 104
<211> LENGTH: 20
<212> TYPE: PRT
<213> ORGANISM: Artificial Sequence
<220> FEATURE:
<223> OTHER INFORMATION: shorth P10 variants
<220> FEATURE:
<221> NAME/KEY: MOD_RES
<222> LOCATION: (1)..(1)
```

```
<223> OTHER INFORMATION: ACETYLATION
<220> FEATURE:
<221> NAME/KEY: MOD_RES
<222> LOCATION: (20)..(20)
<223> OTHER INFORMATION: AMIDATION

<400> SEQUENCE: 104

Leu Ala Arg Glu Tyr Lys Lys Ile Val Glu Lys Leu Lys Arg Trp Leu
1               5                   10                  15

Arg Gln Val Leu
            20

<210> SEQ ID NO 105
<211> LENGTH: 18
<212> TYPE: PRT
<213> ORGANISM: Artificial Sequence
<220> FEATURE:
<223> OTHER INFORMATION: shorth P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (18)..(18)
<223> OTHER INFORMATION: AMIDATION

<400> SEQUENCE: 105

Glu Tyr Lys Lys Ile Val Glu Lys Leu Lys Arg Trp Leu Arg Gln Val
1               5                   10                  15

Leu Arg

<210> SEQ ID NO 106
<211> LENGTH: 16
<212> TYPE: PRT
<213> ORGANISM: Artificial Sequence
<220> FEATURE:
<223> OTHER INFORMATION: shorth P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (16)..(16)
<223> OTHER INFORMATION: AMIDATION

<400> SEQUENCE: 106

Tyr Lys Lys Ile Val Glu Lys Leu Lys Arg Trp Leu Arg Gln Val Leu
1               5                   10                  15

<210> SEQ ID NO 107
<211> LENGTH: 13
<212> TYPE: PRT
<213> ORGANISM: Artificial Sequence
<220> FEATURE:
<223> OTHER INFORMATION: shorth P10 variants
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: AMIDATION

<400> SEQUENCE: 107

Lys Lys Ile Val Glu Lys Leu Lys Arg Trp Leu Arg Gln
1               5                   10
```

-continued

```
<210> SEQ ID NO 108
<211> LENGTH: 24
<212> TYPE: PRT
<213> ORGANISM: Artificial Sequence
<220> FEATURE:
<223> OTHER INFORMATION: Synthesized sequence
<220> FEATURE:
<221> NAME/KEY: MISC_FEATURE
<222> LOCATION: (1)..(1)
<223> OTHER INFORMATION: Xaa can be nothing or Leu, Ile, Val, or Ala
<220> FEATURE:
<221> NAME/KEY: MISC_FEATURE
<222> LOCATION: (2)..(2)
<223> OTHER INFORMATION: Xaa can be nothing or Ala, Leu, Val, Ile, or
      Gln
<220> FEATURE:
<221> NAME/KEY: MISC_FEATURE
<222> LOCATION: (3)..(3)
<223> OTHER INFORMATION: Xaa can be nothing or Arg, Lys, or His
<220> FEATURE:
<221> NAME/KEY: MISC_FEATURE
<222> LOCATION: (4)..(4)
<223> OTHER INFORMATION: Xaa can be nothing or Glu or Gln
<220> FEATURE:
<221> NAME/KEY: MISC_FEATURE
<222> LOCATION: (5)..(5)
<223> OTHER INFORMATION: Xaa can be Tyr, Trp, or Phe
<220> FEATURE:
<221> NAME/KEY: MISC_FEATURE
<222> LOCATION: (6)..(6)
<223> OTHER INFORMATION: Xaa can be Arg, His, or Lys
<220> FEATURE:
<221> NAME/KEY: MISC_FEATURE
<222> LOCATION: (7)..(7)
<223> OTHER INFORMATION: Xaa can be Arg, His, or Lys
<220> FEATURE:
<221> NAME/KEY: MISC_FEATURE
<222> LOCATION: (8)..(8)
<223> OTHER INFORMATION: Xaa can be Ile, Ala, Val, or Leu
<220> FEATURE:
<221> NAME/KEY: MISC_FEATURE
<222> LOCATION: (9)..(9)
<223> OTHER INFORMATION: Xaa can be Ile, Ala, Val, or Leu
<220> FEATURE:
<221> NAME/KEY: MISC_FEATURE
<222> LOCATION: (10)..(10)
<223> OTHER INFORMATION: Xaa can be Glu or Gln
<220> FEATURE:
<221> NAME/KEY: MISC_FEATURE
<222> LOCATION: (11)..(11)
<223> OTHER INFORMATION: Xaa can be Lys, Arg, or His
<220> FEATURE:
<221> NAME/KEY: MISC_FEATURE
<222> LOCATION: (12)..(12)
<223> OTHER INFORMATION: Xaa can be Leu, Ile, Val, or Ala
<220> FEATURE:
<221> NAME/KEY: MISC_FEATURE
<222> LOCATION: (13)..(13)
<223> OTHER INFORMATION: Xaa can be Lys, Arg, or His
<220> FEATURE:
<221> NAME/KEY: MISC_FEATURE
<222> LOCATION: (14)..(14)
<223> OTHER INFORMATION: Xaa can be Arg, His, or Lys
<220> FEATURE:
<221> NAME/KEY: MISC_FEATURE
<222> LOCATION: (15)..(15)
<223> OTHER INFORMATION: Xaa can be Trp, Phe or Tyr
<220> FEATURE:
<221> NAME/KEY: MISC_FEATURE
<222> LOCATION: (17)..(17)
<223> OTHER INFORMATION: Xaa can be Arg, Lys, or His
<220> FEATURE:
<221> NAME/KEY: MISC_FEATURE
<222> LOCATION: (18)..(18)
<223> OTHER INFORMATION: Xaa can be Gln, Asn, Ala, Ser, or Thr
<220> FEATURE:
<221> NAME/KEY: MISC_FEATURE
<222> LOCATION: (19)..(19)
```

```
<223> OTHER INFORMATION: Xaa can be Val, Ile, Ala or Leu
<220> FEATURE:
<221> NAME/KEY: MISC_FEATURE
<222> LOCATION: (20)..(20)
<223> OTHER INFORMATION: Xaa can be Leu, Ile, Val, or Ala
<220> FEATURE:
<221> NAME/KEY: MISC_FEATURE
<222> LOCATION: (21)..(21)
<223> OTHER INFORMATION: Xaa can be nothing or Arg, Lys, or His
<220> FEATURE:
<221> NAME/KEY: MISC_FEATURE
<222> LOCATION: (22)..(22)
<223> OTHER INFORMATION: Xaa can be nothing or Thr, Gln, Asn, or Ala
<220> FEATURE:
<221> NAME/KEY: MISC_FEATURE
<222> LOCATION: (23)..(23)
<223> OTHER INFORMATION: Xaa can be nothing or Leu
<220> FEATURE:
<221> NAME/KEY: MISC_FEATURE
<222> LOCATION: (24)..(24)
<223> OTHER INFORMATION: Xaa can be nothing or Arg, Lys, or His

<400> SEQUENCE: 108

Xaa Xaa Xaa Xaa Xaa Xaa Xaa Xaa Xaa Xaa Xaa Xaa Xaa Xaa Xaa Leu
1               5                   10                  15

Xaa Xaa Xaa Xaa Xaa Xaa Xaa Xaa
            20

<210> SEQ ID NO 109
<211> LENGTH: 24
<212> TYPE: PRT
<213> ORGANISM: Artificial Sequence
<220> FEATURE:
<223> OTHER INFORMATION: Synthesized sequence
<220> FEATURE:
<221> NAME/KEY: MISC_FEATURE
<222> LOCATION: (1)..(1)
<223> OTHER INFORMATION: Xaa can be nothing or Leu, Ile, Val, or Ala
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa can be nothing or Ala, Leu, Val, Ile, or
      Gln
<220> FEATURE:
<221> NAME/KEY: MISC_FEATURE
<222> LOCATION: (3)..(3)
<223> OTHER INFORMATION: Xaa can be nothing or Arg, Lys, or His
<220> FEATURE:
<221> NAME/KEY: MISC_FEATURE
<222> LOCATION: (4)..(4)
<223> OTHER INFORMATION: Xaa can be nothing or Glu or Gln
<220> FEATURE:
<221> NAME/KEY: MISC_FEATURE
<222> LOCATION: (5)..(5)
<223> OTHER INFORMATION: Xaa can be Tyr, Trp, or Phe
<220> FEATURE:
<221> NAME/KEY: MISC_FEATURE
<222> LOCATION: (6)..(6)
<223> OTHER INFORMATION: Xaa can be Arg, His, or Lys
<220> FEATURE:
<221> NAME/KEY: MISC_FEATURE
<222> LOCATION: (7)..(7)
<223> OTHER INFORMATION: Xaa can be Arg, His, or Lys
<220> FEATURE:
<221> NAME/KEY: MISC_FEATURE
<222> LOCATION: (8)..(8)
<223> OTHER INFORMATION: Xaa can be Ile, Ala, Val, or Leu
<220> FEATURE:
<221> NAME/KEY: MISC_FEATURE
<222> LOCATION: (9)..(9)
<223> OTHER INFORMATION: Xaa can be Ile, Ala, Val, or Leu
<220> FEATURE:
```

```
<221> NAME/KEY: MISC_FEATURE
<222> LOCATION: (10)..(10)
<223> OTHER INFORMATION: Xaa can be Glu or Gln
<220> FEATURE:
<221> NAME/KEY: MISC_FEATURE
<222> LOCATION: (11)..(11)
<223> OTHER INFORMATION: Xaa can be Lys, Arg, or His
<220> FEATURE:
<221> NAME/KEY: MISC_FEATURE
<222> LOCATION: (12)..(12)
<223> OTHER INFORMATION: Xaa can be Leu, Ile, Val, or Ala
<220> FEATURE:
<221> NAME/KEY: MISC_FEATURE
<222> LOCATION: (13)..(13)
<223> OTHER INFORMATION: Xaa can be Lys, Arg, or His
<220> FEATURE:
<221> NAME/KEY: MISC_FEATURE
<222> LOCATION: (14)..(14)
<223> OTHER INFORMATION: Xaa can be Arg, His, or Lys
<220> FEATURE:
<221> NAME/KEY: MISC_FEATURE
<222> LOCATION: (15)..(15)
<223> OTHER INFORMATION: Xaa can be Trp, Phe or Tyr
<220> FEATURE:
<221> NAME/KEY: MISC_FEATURE
<222> LOCATION: (17)..(17)
<223> OTHER INFORMATION: Xaa can be Arg, Lys, or His
<220> FEATURE:
<221> NAME/KEY: MISC_FEATURE
<222> LOCATION: (18)..(18)
<223> OTHER INFORMATION: Xaa can be Gln, Asn, Ala, Ser, or Thr
<220> FEATURE:
<221> NAME/KEY: MISC_FEATURE
<222> LOCATION: (19)..(19)
<223> OTHER INFORMATION: Xaa can be Val, Ile, Ala or Leu
<220> FEATURE:
<221> NAME/KEY: MISC_FEATURE
<222> LOCATION: (20)..(20)
<223> OTHER INFORMATION: Xaa can be Leu, Ile, Val, or Ala
<220> FEATURE:
<221> NAME/KEY: MISC_FEATURE
<222> LOCATION: (21)..(21)
<223> OTHER INFORMATION: Xaa can be nothing or Arg, Lys, or His
<220> FEATURE:
<221> NAME/KEY: MISC_FEATURE
<222> LOCATION: (22)..(22)
<223> OTHER INFORMATION: Xaa can be nothing or Thr, Gln, Asn, or Ala
<220> FEATURE:
<221> NAME/KEY: MISC_FEATURE
<222> LOCATION: (23)..(23)
<223> OTHER INFORMATION: Xaa can be nothing or Leu
<220> FEATURE:
<221> NAME/KEY: MISC_FEATURE
<222> LOCATION: (24)..(24)
<223> OTHER INFORMATION: Xaa can be nothing or Arg, Lys, or His
<220> FEATURE:
<221> NAME/KEY: MOD_RES
<222> LOCATION: (24)..(24)
<223> OTHER INFORMATION: AMIDATION

<400> SEQUENCE: 109

Xaa Xaa Xaa Xaa Xaa Xaa Xaa Xaa Xaa Xaa Xaa Xaa Xaa Xaa Xaa Leu
1               5                   10                  15

Xaa Xaa Xaa Xaa Xaa Xaa Xaa Xaa
            20

<210> SEQ ID NO 110
<211> LENGTH: 24
<212> TYPE: PRT
<213> ORGANISM: Artificial Sequence
<220> FEATURE:
<223> OTHER INFORMATION: antimicrobial peptide - synthesized sequence
<220> FEATURE:
<221> NAME/KEY: MOD_RES
<222> LOCATION: (1)..(1)
<223> OTHER INFORMATION: ACETYLATION
```

```
<220> FEATURE:
<221> NAME/KEY: MOD_RES
<222> LOCATION: (24)..(24)
<223> OTHER INFORMATION: AMIDATION

<400> SEQUENCE: 110

Leu Ala Arg Glu Tyr Lys Lys Ile Val Glu Lys Leu Lys Arg Trp Leu
1               5                   10                  15

Arg Gln Val Leu Arg Thr Leu Arg
            20

<210> SEQ ID NO 111
<211> LENGTH: 24
<212> TYPE: PRT
<213> ORGANISM: Artificial Sequence
<220> FEATURE:
<223> OTHER INFORMATION: antimicrobial peptide
<220> FEATURE:
<221> NAME/KEY: MISC_FEATURE
<222> LOCATION: (6)..(6)
<223> OTHER INFORMATION: Xaa can be Pro or Lys
<220> FEATURE:
<221> NAME/KEY: MISC_FEATURE
<222> LOCATION: (7)..(7)
<223> OTHER INFORMATION: Xaa can be Pro or Lys
<220> FEATURE:
<221> NAME/KEY: MISC_FEATURE
<222> LOCATION: (8)..(8)
<223> OTHER INFORMATION: Xaa can be Pro or Ile
<220> FEATURE:
<221> NAME/KEY: MISC_FEATURE
<222> LOCATION: (10)..(10)
<223> OTHER INFORMATION: Xaa can be Pro or Glu
<220> FEATURE:
<221> NAME/KEY: MISC_FEATURE
<222> LOCATION: (16)..(16)
<223> OTHER INFORMATION: Xaa can be Pro or Leu
<220> FEATURE:
<221> NAME/KEY: MISC_FEATURE
<222> LOCATION: (18)..(18)
<223> OTHER INFORMATION: Xaa can be Pro or Gln
<220> FEATURE:
<221> NAME/KEY: MISC_FEATURE
<222> LOCATION: (20)..(20)
<223> OTHER INFORMATION: Xaa can be Pro or Leu

<400> SEQUENCE: 111

Leu Ala Arg Glu Tyr Xaa Xaa Xaa Val Xaa Lys Leu Lys Arg Trp Xaa
1               5                   10                  15

Arg Xaa Val Xaa Arg Thr Leu Arg
            20

<210> SEQ ID NO 112
<211> LENGTH: 24
<212> TYPE: PRT
<213> ORGANISM: Artificial Sequence
<220> FEATURE:
<223> OTHER INFORMATION: antimicrobial peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(24)
<223> OTHER INFORMATION: contains functional groups hexanoyl, decanoyl,
      myristoyl, propionyl, amino-hexanoyl, or NH-(CH2-CH2-O)11-CO
<220> FEATURE:
<221> NAME/KEY: MOD_RES
<222> LOCATION: (24)..(24)
<223> OTHER INFORMATION: AMIDATION

<400> SEQUENCE: 112
```

Leu Ala Arg Glu Tyr Lys Lys Ile Val Glu Lys Leu Lys Arg Trp Leu
1               5                   10                  15

Arg Gln Val Leu Arg Thr Leu Arg
            20

<210> SEQ ID NO 113
<211> LENGTH: 24
<212> TYPE: PRT
<213> ORGANISM: Artificial Sequence
<220> FEATURE:
<223> OTHER INFORMATION: antimicrobial peptide
<220> FEATURE:
<221> NAME/KEY: MISC_FEATURE
<222> LOCATION: (1)..(1)
<223> OTHER INFORMATION: Xaa can be nothing or Leu
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa can be nothing or Ala
<220> FEATURE:
<221> NAME/KEY: MISC_FEATURE
<222> LOCATION: (3)..(3)
<223> OTHER INFORMATION: Xaa can be nothing or Arg
<220> FEATURE:
<221> NAME/KEY: MISC_FEATURE
<222> LOCATION: (4)..(4)
<223> OTHER INFORMATION: Xaa can be nothing or Glu
<220> FEATURE:
<221> NAME/KEY: MISC_FEATURE
<222> LOCATION: (5)..(5)
<223> OTHER INFORMATION: Xaa can be nothing or Tyr
<220> FEATURE:
<221> NAME/KEY: MISC_FEATURE
<222> LOCATION: (19)..(19)
<223> OTHER INFORMATION: Xaa can be nothing or Val
<220> FEATURE:
<221> NAME/KEY: MISC_FEATURE
<222> LOCATION: (20)..(20)
<223> OTHER INFORMATION: Xaa can be nothing or Leu
<220> FEATURE:
<221> NAME/KEY: MISC_FEATURE
<222> LOCATION: (21)..(21)
<223> OTHER INFORMATION: Xaa can be nothing or Arg
<220> FEATURE:
<221> NAME/KEY: MISC_FEATURE
<222> LOCATION: (22)..(22)
<223> OTHER INFORMATION: Xaa can be nothing or Thr
<220> FEATURE:
<221> NAME/KEY: MISC_FEATURE
<222> LOCATION: (23)..(23)
<223> OTHER INFORMATION: Xaa can be nothing or Leu
<220> FEATURE:
<221> NAME/KEY: MISC_FEATURE
<222> LOCATION: (24)..(24)
<223> OTHER INFORMATION: Xaa can be nothing or Arg
<220> FEATURE:
<221> NAME/KEY: MOD_RES
<222> LOCATION: (24)..(24)
<223> OTHER INFORMATION: AMIDATION

<400> SEQUENCE: 113

Xaa Xaa Xaa Xaa Xaa Lys Lys Ile Val Glu Lys Leu Lys Arg Trp Leu
1               5                   10                  15

Arg Gln Xaa Xaa Xaa Xaa Xaa Xaa
            20

ANTIMICROBIAL PEPTIDE

CROSS-REFERENCE TO RELATED APPLICATIONS

This application is a national phase entry under 35 U.S.C. §371 of International Patent Application PCT/NL2014/050295, filed May 9, 2014, designating the United States of America and published in English as International Patent Publication WO 2014/182172 A1 on Nov. 13, 2014, which claims the benefit under Article 8 of the Patent Cooperation Treaty and under 35 U.S.C. §119(e) to European Patent Application Serial No. 13167240.4, filed May 10, 2013, the disclosure of each of which is hereby incorporated herein in its entirety by this reference.

STATEMENT ACCORDING TO 37 C.F.R. §1.821(c) or (e)—SEQUENCE LISTING SUBMITTED AS A TXT AND PDF FILES

Pursuant to 37 C.F.R. §1.821(c) or (e), files containing a TXT version and a PDF version of the Sequence Listing have been submitted concomitant with this application, the contents of which are hereby incorporated by reference.

TECHNICAL FIELD

The disclosure relates to the field of biochemistry. More specifically, the disclosure relates to the field of antimicrobial peptides and to counteracting bacterial, viral, fungal and parasitic infections.

BACKGROUND

Antimicrobial Peptides (AMPs) are an essential component of the defense system of organisms throughout nature and offer protection against invading pathogens. AMPs do not target single defined molecular structures (epitopes), but act on the cell membrane, thus killing bacteria and fungi rapidly. Therefore, as opposed to conventional antibiotics, they are effective regardless of the metabolic activity of bacteria. In addition to their direct microbicidal activities, antimicrobial peptides are particularly attractive as certain peptides show multiple activities such as the regulation of the innate and adaptive immune systems, inflammation and wound healing, and additional antifungal, antiviral, antiparasitic and anticancerous activities. AMPs are quite diverse in sequence and secondary structure, but share some common properties. They are usually short (about 15 to 40 amino acids), cationic, amphipathic and exert their microbicidal effect mostly by compromising the bacterial membrane integrity. Interaction of AMPs with the anionic membrane surface of the target microbes leads to membrane permeabilization, cell lysis and death. It is generally accepted that the cytoplasmic membrane is the main target of most antimicrobial peptides, whereby accumulation of peptide in the membrane causes increased permeability and loss of barrier function, resulting in leakage of cytoplasmic components and cell death. Various molecular mechanisms for membrane permeabilization, some phenomenological and others more quantitative, have been proposed to explain the action of AMPs.

Experimental observations in model systems were mainly rationalized by the carpet or pore model (FIG. 1). In the carpet model, AMPs accumulate on the membrane surface oriented in a parallel fashion to the membrane, resulting in local membrane thinning and destabilization of the cell membrane leading to the release of intracellular content. However, there is compelling evidence that many AMPs also function in a detergent-like manner, by disrupting the packing and organization of the lipids in a nonspecific way (e.g., lipid clustering or segregation of polar and nonpolar groups of the lipids) or by inducing non-bilayer lipid aggregates. Moreover, some AMPs pass the cell membrane and interact with an intracellular target (FIG. 1), leading to loss of bacterial/fungal viability.

Clearly, the mode(s) of action of AMPs differ from those of conventional antibiotics, which often have simple targets, such as a unique epitope on the cell wall, or in the protein and RNA synthesis processes, allowing the pathogenic bacteria to develop resistance more rapidly. A major advantage of antimicrobial peptides over conventional antibiotics is that microbial resistance against these AMPs does not readily develop, most likely because these peptides—in contrast to conventional antibiotics—do not target single defined molecular structures (epitopes), but act on the cell membrane, thus killing bacteria and fungi within minutes. Thus, owing to the fast killing rate, being faster than the growth rate of bacteria, and nature of the target (substantial modification of the lipid composition would affect bacterial cell viability), resistance development is less likely. The emergence of mutants being resistant to AMPs has been determined by monitoring bacterial susceptibility after repeated sub-culturing in the presence of sub-inhibitory concentrations of the peptides, showing that the mutation rate was lower than other clinical antibiotics tested (e.g., ciprofloxacin and erythromycin). While the Minimal Inhibiting Concentration (MIC) of those antibiotics increased through all the subcultures (up to 64 times), the pressure of the peptides did not increase the MIC of the strain. Thus, in contrast to conventional antibiotics, resistance development in the presence of AMPs is less unlikely to occur. Furthermore, AMPs are fast-acting and biodegradable, which alleviates the current concern about residual antibiotics in the environment.

A wide variety of microbial infections are associated with biofilm formation, where microorganisms aggregate in a structured community in a self-produced polymeric matrix and adhere to a surface. An additional disadvantage of conventional antibiotics is that they do not ensure eradication of biofilm infections for the following reasons:

1) Insufficient penetration of conventional antibiotics into biofilms: The matrix in which bacteria are embedded protects them from external influences, such as antimicrobial substances. Most antibiotics are able to penetrate the biofilm, but their diffusion into the biofilm is slow so that they are inactivated before they can elicit their desired effect.

2) Low metabolic activity of bacteria: Biofilm-associated infections (BAI) are usually treated with vancomycin, often in combination with rifampicin. Although vancomycin is known to penetrate biofilms rather well—albeit at a significantly reduced transport rate—it poorly reduces the number of bacteria residing within the biofilm. Treatment with this antibiotic still has, therefore, a relatively high rate of failure, which can be explained by the low metabolic activity of bacteria in the biofilm, rendering the antibiotic ineffective.

3) Inactivation or degradation of the antibiotics: In BAI, antibiotics are mostly administered systemically. Therefore, they are prone to be removed from the bloodstream by renal clearance and degraded enzymatically in the blood and surrounding tissues. Enzymes (produced by bacteria) can directly destruct or modify the compound. These mechanisms actively reduce the concentration of drugs in the local environment. In biofilms, the low penetration poses an additional problem. Increasing the systemically administered concentration is not feasible due to the toxicity of high blood concentrations of antibiotics.

4) Bacteria have developed resistance: On top of the general increase of bacterial resistance to antibiotics, due to the decreased concentrations of antibiotics in the deeper layers, the risk that bacteria escape from antibiotic pressure is higher, which may lead to the survival of mutants that have increased resistance to these antibiotics. It has even been reported that suboptimal concentrations of antibiotics, including vancomycin, enhance biofilm formation. Moreover, repetitive administration of conventional antibiotics that have an insufficient effect promotes the development of antibiotic resistance.

5) Conventional antibiotics cause the release of pro-inflammatory microbial compounds: It has been shown that in BAI, peri-implant tissue is colonized by bacteria. To a large extent, this is due to the deregulation of the local immune response. This is the reason why, in many cases, the infection persists, even after replacement of the implant. Implantation of a biomaterial provokes an inflammatory response known as the "foreign body response," characterized by sequential influx of neutrophils, macrophages/monocytes and lymphocytes, followed by fusion of macrophages to multinucleated foreign body giant cells lining the biomaterial, novel fibroblast foiination and deposition of fibrin, leading to fibrosis/encapsulation of the foreign body. This sequence of events is highly regulated by molecular signals such as cytokines produced by the cell types involved. In case of infection, the host immune system is additionally triggered by molecules of the bacteria designated as "Pathogen-Associated Molecular Patterns" (PAMPs) recognized by specific receptors on the host cells, such as Toll-Like Receptors (TLRs). For example, bacterial peptidoglycan or lipopolysaccharide are recognized by TLR2 and TLR4, and are potent inducers of inflammatory responses. The activation of the immune system, both by the foreign body response and the bacterial infection, leads to an "over-the-top" reaction of the host immune system, leading to inflamed and disrupted tissue; in fact, providing the ideal environment for infection. Thus, the simultaneous activation by biomaterial and PAMPs can have deleterious effects on immune function and strongly increase susceptibility to infection.

At present, over 2,000 different antimicrobial peptide sequences are known (see, for instance, the World Wide Web at bbcm.univ.trieste.itttossi/search.htm), including cecropins, defensins, magainins and cathelicidins. Antimicrobial peptides and proteins are, for instance, described in:

U.S. Pat. No. 6,503,881, which discloses cationic peptides being an indolicidin analogue to be used as an antimicrobial peptide. The cationic peptides are derived from different species, including animals and plants.

U.S. Pat. No. 5,912,230, which discloses anti-fungal and anti-bacterial histatin-based peptides and methods for treatment of fungal and bacterial infections. The peptides are based on defined portions of the amino acid sequences of naturally occurring human histatins.

U.S. Pat. No. 5,717,064, which discloses methylated lysine-rich lytic peptides. The lytic peptides are tryptic digestion resistant and non-natural. The lytic peptides are suitable for in vivo administration.

U.S. Pat. No. 5,646,014, which discloses an antimicrobial peptide isolated from an antimicrobial fraction from silkworm hemolymph. The peptide exhibits antimicrobial activity against several bacterial strains, such as *Escherichia coli*, *Staphylococcus aureus* and *Bacillus cereus*.

WO 2004/016653, which discloses a peptide based on the 20 to 44 sequence of azurocidin. This peptide contains a loop structure linked by disulfide bridges.

U.S. Pat. No. 6,495,516, which discloses peptides based on the bactericidal 55 kDa protein bactericidal/permeability-increasing protein (BPI). The peptides exert antimicrobial effects as well as having LPS-neutralizing capacity.

WO 01/81578, which discloses numerous sequences encoding G-coupled protein receptor-related polypeptides, which may be used for numerous diseases.

WO 2004/067563 and WO 2005/040192, that disclose antimicrobial peptides based on peptide LL-37, the 37 C-terminal amino acid of the human cathelicidin.

Several AMPs, daptomycin and DPK-060, are currently in clinical use and/or development, e.g., polymyxin B, nisin, pexiganan, omiganan, iseganan. Further, up to phase 2 clinical trials have been performed for OP-145, a 24-amino acid peptide derived from the endogenous human cathelicidin antimicrobial peptide LL-37. OP-145 has been developed as an endotoxin-neutralizing antimicrobial peptide for the topical treatment of chronic otitis media. The currently known AMPs still have a few drawbacks. Although proteolytic degradation is beneficial for the environment (no residual AMPs), it prevents dynamic circulation. This is also caused by efficient peptide clearance. Also, the exact working mechanisms of AMPs remain largely unknown, so it is difficult to foresee their true applications and full potential. For example, it is often not known how AMPs interact with host cells to induce their effects. Therefore, the use of AMPs in clinical indications has been limited to topical applications.

Various bacteria, such as *P. aeruginosa*, *E. faecalis*, *Proteus mirabilis*, *Streptococcus pyogenes* and *S. aureus* all secrete proteases that degrade several antimicrobial peptides, such as the cathelicidin LL-37. Thus, protease-resistant antimicrobial peptides are advantageous from a therapeutical standpoint. Additionally, many of the antimicrobial peptides are not very efficient in challenging microorganisms such as bacteria, e.g., *S. aureus* and *P. aeruginosa*, frequently playing key roles in problematic pathogeneses, and need to be optimized to show an increased effect. Furthermore, due to potential lytic as well as other properties of AMPs against bacterial as well as mammalian membranes, one of the challenges in designing new peptides relies on developing AMPs with high specificity against microorganisms such as bacterial or fungal cells as compared to cellular membranes of the infected patient, i.e., a high therapeutic index (minimal hemolytic concentration/minimal antimicrobial activity; MHC/MEC).

Therefore, even though there are a relatively large number of antimicrobial peptides available today, there is still an increased need of new improved antimicrobial peptides, which can be used to counteract microbes, in particular, those that are resistant or tolerant against antibiotic agents and/or other antimicrobial agents. More importantly, there is a need for new antimicrobial peptides, which are non-allergenic when introduced into mammals such as human beings and that have high specificity against pathogenic microorganisms.

BRIEF SUMMARY

Provided is a novel potent antimicrobial peptide that overcomes the shortcomings of conventional antibiotics and that has improved properties over known antimicrobial peptides. Also provided is a novel peptide that exerts high activity against pathogenic microorganisms in biofilm infections.

It has been found that polypeptide P10, having the sequence LAREYKKIVEKLKRWLRQVLRTLR (SEQ ID NO:1), is highly effective against (drug-resistant) gram-positive (e.g., *Staphylococcus aureus*) and gram-negative (e.g., *Pseudomonas aeruginosa*) bacteria as well as against fungi, e.g., *Candida albicans* and *Aspergillus niger* in vitro. As is shown in FIGS. 2A and 2B, P10 is considerably more effective than any other peptide tested. In addition, P10 is able to prevent methicillin-resistant *S. aureus* biofilm formation on plastic as well as biotic (wounded 3-D human skin model) surfaces. Moreover, P10 neutralizes endotoxin lipoteichoic acid (LTA), peptidoglycan (PG) and lipopolysaccharides (LPS), thus reducing the proinflammatory response. P10 adopts an α-helix resulting in an amphipathic structure in which polar amino acids are located at one side of the helix and lipophilic amino acids at the opposite side. Peptides in which proline substitutions were introduced to break the helix were inactive, indicating that the amphipathic nature of the polypeptide is important for its biological activities. P10 was found to be even considerably more potent than OP-145 (P60.4Ac) for which clinical trials have been performed as is apparent from FIGS. 2-5. As is shown in FIG. 2B and detailed in the Examples, P10 has an IC99.9 (0.59 µM) that is even lower than the IC90 of P60.4Ac (0.75 µM). Thus, at a concentration of 0.59 µM, P10 kills 999 out of 1000 bacteria, whereas P60.4Ac kills only 900 out of 1000 bacteria at a similar, even slightly higher concentration. Thus, 100 times more bacteria survive after treatment with P60.4Ac as compared to treatment with P10 at a similar concentration. Moreover, P10 has a broad activity spectrum, as it is active against a wide variety of microorganisms including bacteria, fungi, viruses and parasites.

The unique effect of the antimicrobial peptides of the disclosure on biofilm infections is three-fold: they will 1) prevent biofilm formation and disperse existing biofilms, 2) kill the bacteria, fungi or other microbes at and around the site of release, and 3) orchestrate immune responses by neutralizing pro-inflammatory microbial endotoxins such as lipoteichoic acid (LTA), peptidoglycan (PG) and lipopolysaccharides (LPS) and activating macrophages to enhance their phagocytic and microbicidal activity. This immune control is necessary to prevent the tissue surrounding implants to become a novel niche for the pathogens. The polypeptides of the disclosure are active against a wide range of micro-organisms, including those that are resistant to conventional antibiotics.

It was further found that i) P10 variants in which one or all amino acids have been replaced by its D-amino acid (Table 2), ii) P-10 variants in which the peptide has been elongated N-terminally or C-terminally with different groups including acetyl, amide, NH—(CH$_2$—CH$_2$—O)$_{11}$—CO, hexanoyl, decanoyl, myristoyl, propionyl, one or two amino-hexanoyl groups, iii) P-10 variants in which one amino acid has been replaced by another L-amino acid, and iv) shorter P-10 variants have antimicrobial activity that is comparable to that of P10, as is demonstrated in the Examples (see Tables 2, 3, 5 and 6).

Hence, a polypeptide according to this disclosure has high antimicrobial activity against microorganisms, either residing in biofilms or not, with optimal anti-inflammatory (microbial compound-neutralizing) activity as evidenced by endotoxin-neutralizing activity, high selectivity, i.e., a high antimicrobial activity, an acceptable low cytotoxicity and immune-enhancing activity.

Accordingly, this disclosure provides an isolated or recombinant polypeptide comprising an amino acid sequence LAREYKKIVEKLKRWLRQVLRTLR (SEQ ID NO:1), or a variant of the amino acid sequence, said polypeptide having antimicrobial, antibacterial, antiviral, antifungal, antiparasitic and/or anti-inflammatory activity, the variant having at least 16 amino acids and:

having up to 5 of the following amino acid substitutions:
substitution of one or more amino acids selected from the group of L, I, V or A by another amino acid selected from the group;
substitution of one or more amino acids selected from the group of R, K or H by another amino acid selected from the group;
substitution of E by Q
substitution of Y or W by F
substitution of one or more amino acids selected from the group of Q, N, A, S or T by another amino acid selected from the group having one or more substitutions of an amino acid by a corresponding D-amino acid, having one or more substitutions of an amino acid by a corresponding non-natural amino acid, and/or having a retro-inverso sequence of at least 16 consecutive amino acids from the amino acid sequence.

In amino acid sequences or variants thereof as defined herein, amino acids are denoted by single-letter symbols. These single-letter symbols and three-letter symbols are well known to the person skilled in the art and have the following meaning: A (Ala) is alanine, C (Cys) is cysteine, D (Asp) is aspartic acid, E (Glu) is glutamic acid, F (Phe) is phenylalanine, G (Gly) is glycine, H (His) is histidine, I (Ile) is isoleucine, K (Lys) is lysine, L (Leu) is leucine, M (Met) is methionine, N (Asn) is asparagine, P (Pro) is proline, Q (Gln) is glutamine, R (Arg) is arginine, S (Ser) is serine, T (Thr) is threonine, V (Val) is valine, W (Trp) is tryptophan, and Y (Tyr) is tyrosine.

A polypeptide of the disclosure has antimicrobial activity, preferably antibacterial, antiviral and/or antifungal activity, more preferably anti-bacterial and/or antifungal activity. Further, a polypeptide of the disclosure preferably has both antimicrobial and anti-inflammatory activity. The term "antimicrobial activity" of a polypeptide as used herein refers to counteracting growth or proliferation of at least one microbe, e.g., a bacterium, a virus and/or a fungus, and includes inhibition, reduction or prevention of growth or proliferation as well as killing of the microbe. A microbe is an organism that is microscopic, i.e., usually too small to be seen by the naked human eye. Microbes are very diverse; they include bacteria, viruses, fungi, archaea, protozoans and microscopic algae. Similarly, the term "antibacterial activity," "antiviral activity," "antifungal activity" and "antiparasitic activity" as used herein refers to counteracting growth or proliferation of, respectively, a bacterium, a virus, a fungus and a parasite, in general, and includes inhibition, reduction or prevention of growth or proliferation as well as killing thereof Antimicrobial, antibacterial, antiviral, antifungal and antiparasitic activity can be measured by methods known in the art.

One of these methods is detailed in the Examples of this application and involves an in vitro killing assay. In this method, microbes (e.g., bacteria or fungi) are incubated for 1 to 2 hours with different concentrations of a polypeptide according to the disclosure. After the microbe-polypeptide mixture is incubated in a suitable culture medium, the number of surviving and/or dead microbes is compared to a sample of microbes, which was not incubated with the polypeptide.

Virus plaque assays may be used to assess the antiviral activity of a polypeptide of the disclosure. In short, a virus inoculum is exposed to the polypeptide prior to infection of a permissive cell monolayer. After a standard interval, the virus titer in the cellular extracts is determined using multiple dilutions of these extracts by infecting fresh cell monolayers and quantifying their effects on the cell monolayer.

For assessment of antiparasitic activity, a polypeptide of the disclosure and a parasite are incubated for a standard time interval. Thereafter, the metabolic activity of the parasites may be analyzed directly, for instance, by an MTT assay, or the parasites are transferred to mammalian cells and after incubation, parasite multiplication in these cells is assessed by microscopy.

The term "anti-inflammatory activity" of a polypeptide as used herein refers to inhibiting, reducing or preventing an inflammatory response in a subject that has been infected by microbes, e.g., bacteria, viruses, fungi, and/or parasites. Anti-inflammatory activity of polypeptides of the disclosure is achieved by inhibiting, reducing or preventing the release of pro-inflammatory microbial compounds, such as lipoteichoic acid (LTA), peptidoglycan (PG) and/or lipopolysaccharides (LPS). Anti-inflammatory activity can be measured by methods known in the art. One example of such method is a lipopolysaccharide neutralization assay. In this method, a polypeptide of the disclosure is mixed with 1 mg of lipopolysaccharides and incubated for 60 minutes. Thereafter, these mixtures were added to 4 times diluted fresh human blood and 18 hours thereafter, the level of cytokines (1L-8, 1L-12p40) in the blood sample are measured by ELISA.

A variant of amino acid sequence LAREYKKIVEKLKRWLRQVLRTLR (SEQ ID NO:1) as used herein has a length of at least 16 amino acids and preferably has up to 5 of the following amino acid substitutions:
  substitution of one or more amino acids selected from the group of L, I, V or A by another amino acid selected from the group;
  substitution of one or more amino acids selected from the group of R, K or H by another amino acid selected from the group;
  substitution of E by Q
  substitution of Y or W by F
  substitution of one or more amino acids selected from the group of Q, N, A, S or T by another amino acid selected from the group
  substitution of one or more amino acids by the corresponding D-amino acid
  substitution of one or more amino acids by a corresponding non-natural amino acid. The variant may have 1, 2, 3, 4, or 5 of the substitutions of an L-amino acid by another L-amino acid and/or of an L-amino acid by its corresponding D-amino acid. Alternatively, all, or at least 16, L-amino acids of the variant are substituted by its corresponding D-amino acid.

Preferably the variant has up to 5 of the following amino acid substitutions:
  substitution of L at amino acid position 1 by I, V or A
  substitution of A at amino acid position 2 by L, V, Q or I
  substitution of R at amino acid position 3 by K or H
  substitution of E at amino acid position 4 by Q
  substitution of Y at amino acid position 5 by F or W
  substitution of K at amino acid position 6 by R or H
  substitution of K at amino acid position 7 by R or H
  substitution of I at amino acid position 8 by L, V or A
  substitution of V at amino acid position 9 by L, I or A
  substitution of E at amino acid position 10 by Q
  substitution of K at amino acid position 11 by R or H
  substitution of L at amino acid position 12 by I, V or A
  substitution of K at amino acid position 13 by R or H
  substitution of R at amino acid position 14 by K or H
  substitution of W at amino acid position 15 by F or Y
  substitution of R at amino acid position 17 by H or K
  substitution of Q at amino acid position 18 by N, A, S or T
  substitution of V at amino acid position 19 by L, I or A
  substitution of L at amino acid position 20 by I, V or A
  substitution of R at amino acid position 21 by K or H
  substitution of T at amino acid position 22 by Q, N or A
  substitution of R at amino acid position 24 by H or K
  substitution of 1 to 5 amino acids by a corresponding D-amino acid. Herein, the numbering of amino acids is as follows:
$L_1 \quad A_2R_3E_4Y_5K_6K_7I_8V_9E_{10}K_{11}L_{12}K_{13}R_{14}W_{15}L_{16}\text{-}R_{17}Q_{18}V_{19}L_{20}R_{21}T_{22}I_{23}R_{24}$.

Preferably, a variant as defined herein has up to 4 of the amino acid substitutions, more preferably up to 3 of the amino acid substitutions, such as 1, 2, 3, 4 or 5 of the substitutions. Further, a variant as defined herein preferably comprises at least an amino acid sequence YKKIVEKLKRWLRQVL (SEQ ID NO:2) having up to 5, more preferably up to 4, most preferably up to 3 of the amino acid substitutions.

The up to 5 amino acid substitutions in the variant of an L amino acid by another L amino acid are preferably the following:
  substitution of L at amino acid position 1 by I, V or A
  substitution of A at amino acid position 2 by L, V or Q
  substitution of R at amino acid position 3 by K or H
  substitution of E at amino acid position 4 by Q
  substitution of Y at amino acid position 5 by F
  substitution of K at amino acid position 6 by R or H
  substitution of K at amino acid position 7 by R or H
  substitution of K at amino acid position 11 by R or H
  substitution of L at amino acid position 12 by I, V or A
  substitution of K at amino acid position 13 by H
  substitution of R at amino acid position 14 by K or H
  substitution of W at amino acid position 15 by F
  substitution of R at amino acid position 17 by H
  substitution of Q at amino acid position 18 by N, A, S or T
  substitution of V at amino acid position 19 by L
  substitution of L at amino acid position 20 by I, V or A
  substitution of R at amino acid position 21 by K or H
  substitution of T at amino acid position 22 by Q, N or A
  substitution of R at amino acid position 24 by H.

In another preferred embodiment, a polypeptide according to the disclosure comprises an amino acid sequence selected from the group consisting of:

```
                                      (SEQ ID NO: 1)
         LAREYKKIVEKLKRWLRQVLRTLR (SEQ ID NO: 4)
         IAREYKKIVEKLKRWLRQVLRTLR (SEQ ID NO: 5)
         VAREYKKIVEKLKRWLRQVLRTLR
```

-continued

AAREYKKIVEKLKRWLRQVLRTLR (SEQ ID NO: 6)

LLREYKKIVEKLKRWLRQVLRTLR (SEQ ID NO: 7)

LVREYKKIVEKLKRWLRQVLRTLR (SEQ ID NO: 8)

LQREYKKIVEKLKRWLRQVLRTLR (SEQ ID NO: 9)

LAKEYKKIVEKLKRWLRQVLRTLR (SEQ ID NO: 10)

LAHEYKKIVEKLKRWLRQVLRTLR (SEQ ID NO: 11)

LARQYKKIVEKLKRWLRQVLRTLR (SEQ ID NO: 12)

LAREFKKIVEKLKRWLRQVLRTLR (SEQ ID NO: 13)

LAREYRKIVEKLKRWLRQVLRTLR (SEQ ID NO: 14)

LAREYHKIVEKLKRWLRQVLRTLR (SEQ ID NO: 15)

LAREYKRIVEKLKRWLRQVLRTLR (SEQ ID NO: 16)

LAREYKKIVEKLKKWLRQVLRTLR (SEQ ID NO: 17)

LAREYKKIVEKLKRFLRQVLRTLR (SEQ ID NO: 18)

LAREYKKIVEKLKRWLHQVLRTLR (SEQ ID NO: 19)

LAREYKKIVEKLKRWLRNVLRTLR (SEQ ID NO: 20)

LAREYKKIVEKLKRWLRAVLRTLR (SEQ ID NO: 21)

LAREYKKIVEKLKRWLRSVLRTLR (SEQ ID NO: 22)

LAREYKKIVEKLKRWLRTVLRTLR (SEQ ID NO: 23)

LAREYKKIVEKLKRWLRQLLRTLR (SEQ ID NO: 24)

LAREYKKIVEKLKRWLRQVIRTLR (SEQ ID NO: 25)

LAREYKKIVEKLKRWLRQVVRTLR (SEQ ID NO: 26)

LAREYKKIVEKLKRWLRQVARTLR (SEQ ID NO: 27)

LAREYKKIVEKLKRWLRQVLKTLR (SEQ ID NO: 28)

LAREYKKIVEKLKRWLRQVLHTLR (SEQ ID NO: 29)

LAREYKKIVEKLKRWLRQVLRQLR (SEQ ID NO: 30)

LAREYKKIVEKLKRWLRQVLRNLR (SEQ ID NO: 31)

LAREYKKIVEKLKRWLRQVLRALR (SEQ ID NO: 32)

-continued

LAREYKKIVEKLKRWLRQVLRTLH (SEQ ID NO: 33)

REYKKTVEKLKRWLRQVLRTLR (SEQ ID NO: 34)

LAREYKKIVEKLKRWLRQVLRT (SEQ ID NO: 35)

REYKKIVEKLKRWLRQVLRT (SEQ ID NO: 36)

YKKIVEKLKRWLRQVLRTLR (SEQ ID NO: 37)

LAREYKKIVEKLKRWLRQVL (SEQ ID NO: 38)

EYKKIVEKLKRWLRQVLR (SEQ ID NO: 39)

YKKIVEKLKRWLRQVL, (SEQ ID NO: 40)

optionally having an N-terminal and/or C-terminal modification, preferably comprising an N- and/or C-terminal elongating group, the N-terminal modification preferably selected from the group consisting of an acetyl-, hexanoyl-, decanoyl-, myristoyl-, NH—(CH$_2$—CH$_2$—O)$_{11}$—CO— and propionyl residue and the C-terminal modification preferably selected from the group consisting of amide-, NH—(CH$_2$—CH$_2$—O)$_{11}$—CO-amide- and one or two aminohexanoyl groups. In one embodiment, a polypeptide according to the disclosure consists of one of the amino acid sequences.

Alternatively, or in addition to the up to 5 substitutions of an amino acid by another amino acid as described above, a variant of amino acid sequence LAREYKKIVEKLKRWLRQVLRTLR (SEQ ID NO:1) as defined herein may contain one or more substitutions of an L-amino acid by its corresponding D-amino acid. Amino acids indicated herein by an upper case single-letter symbol, such as A for alanine, are those L-amino acids commonly found in naturally occurring proteins. As demonstrated in the Examples (Table 2), polypeptides wherein an L-amino acid is substituted by its corresponding D-amino acid retain their antimicrobial activity. Therefore, a variant of amino acid sequence LAREYKKIVEKLKRWLRQVLRTLR (SEQ ID NO:1) as defined herein may contain one or more substitutions of an amino acid by the corresponding D-amino acid. "Corresponding D-amino acid" as used herein is defined as the D-amino acid counterpart of an L-amino acid. For example, the corresponding D-amino acid of alanine (A) is D-alanine (a), the corresponding D-amino acid of arginine (R) is D-arginine (r), the corresponding D-amino acid of asparagine (N) is D-asparagine (n), etc. All L-amino acids of a variant as defined herein can be substituted by their corresponding D-amino acids. A variant of amino acid sequence LAREYKKIVEKLKRWLRQVLRTLR (SEQ ID NO:1) as defined herein may contain up to 24 substitutions of an L-amino acid by its corresponding D-amino acid. Hence, the variant may consist entirely of D-amino acids because antimicrobial activity is retained in polypeptides comprising such amino acid variant. For instance, the variant may contain 24, 23, 22, 21, 20, 19, 18, 17, 16, 15, 14, 13, 12, 11, 10, 9, 8, 7, 6 5, 4, 3, 2 or 1 substitutions of an L-amino acid by its corresponding D-amino acid. In one embodiment, a variant of amino acid sequence LAREYKKIVEKLKRWLRQVLRTLR (SEQ ID NO:1) as defined herein contains one substitution of an amino acid by its corresponding D-amino acid. The position of the D-amino acid in the amino acid sequence is irrelevant. As demonstrated in Table 2, in all polypeptides having the sequence LAREYK-KIVEKLKRWLRQVLRTLR (SEQ ID NO:1) wherein one amino acid is substituted by a D-amino acid antimicrobial activity is retained. In another embodiment, the variant contains substitution of all L-amino acids by their corresponding D-amino acid. As also demonstrated in the Examples (Table 2), a polypeptide comprising the sequence lareykkiveklkrwlrqvlrtlr (peptide #1313-07), which is a variant containing only D-amino acids, possesses antimicrobial activity. A "variant" as defined herein may further contain the retro-inverso peptide of at least 16 consecutive amino acids of amino acid sequence LAREYKKIVEKLKRWL-RQVLRTLR (SEQ ID NO:1). Preferably, the variant is a retro-inverso peptide of the full length of the amino acid sequence. A retro-inverso peptide is a peptide consisting of D-amino acids in the reversed sequence of a reference amino acid sequence. Hence, a preferred variant of the disclosure may have at least 16 amino acids of the D-amino acid sequence rltrlvqrlwrklkevikkyeral. As demonstrated in Table 2, a polypeptide comprising the sequence lareykkiveklkrwl-rqvlrtlr (peptide # 1241-03), which is a variant containing the retro-inverso sequence of amino acid sequence LAR-EYKKIVEKLKRWLRQVLRTLR (SEQ ID NO:1), possesses antimicrobial activity.

101421 A variant of amino acid sequence LAREYK-KIVEKLKRWLRQVLRTLR (SEQ ID NO:1) as defined herein may comprise up to 5 substitutions of an amino acid by a non-natural amino acid. "Non-natural amino acids" as used herein refers to non-genetically encoded amino acids, irrespective of whether they appear in nature or not. Non-natural amino acids that can be present in a variant of an amino acid sequence as defined herein include: β-amino acids, p-acyl-L-phenylalanine, N-acetyl lysine, O-4-allyl-L-tyrosine, 2-aminoadipic acid, 3-aminoadipic acid, beta-alanine, 4-tert-butyl hydrogen 2-azidosuccinate, beta-aminopropionic acid, 2-aminobutyric acid, 4-aminobutyric acid, 2,4,-diamino butyric acid, 6-aminocaproic acid, 2-aminoheptanoic acid, 2-aminoisobutyric acid, 3-aminoisobutyric acid, 2-aminopimelic acid, p-aminophenylalanine, 2,3-diaminobutyric acid, 2,3-diamino propionic acid, 2,2'-diaminopimelic acid, p-amino-L-phenylalanine, p-azido-L-phenylalanine, D-allylglycine, p-benzoyl-L-phenylalanine, 3-benzothienyl alanine p-bromophenylalanine, t-butylalanine, t-butylglycine, 4-chlorophenylalanine, cyclohexylalanine, cysteic acid, D-citrulline, thio-L-citrulline, desmosine, epsilon-amino hexanoic acid, N-ethylglycine, N-ethylasparagine, 2-fluorophenylalanine, 3-fluorophenylalanine, 4-fluorophenylalanine, homoarginine, homocysteine, homoserine, hydroxylysine, allo-hydroxylysine, 3-(3-methyl-4-nitrobenzyl)-L-histidine methyl ester, isodesmosine, allo-isoleucine, isopropyl-L-phenylalanine, 3-methylphenylalanine, N-methylglycine, N-methylisoleucine, 6-N-methyllysine, O-methyl-L-tyrosine, N-methylvaline, methionine sulfoxide, 2-napthylalanine, L-3-(2-naphthyl)alanine, isoserine, 3-phenylserine, norvaline, norleucine, 5,5,5-trifluoro-DL-leucine, ornithine, 3-chloro-tyrosine, N5-carbamoylornithine, penicillamine, phenylglycine, piperidinic acid, pyridylalanine, 1,2,3,4-tetrahydro-isoquinoline-3-carboxylix acid, beta-2-thienylalanine, γ-carboxy-DL-glutamic acid, 4-fluoro-DL-glutamic acid, D-thyroxine, allo-threonine, 5-hydroxy-tryptophan, 5-methoxy-tryptophan, 5-fluoro-tryptophan, and 3-fluoro-valine.

In one embodiment, a natural amino acid of the sequence is substituted by a corresponding non-natural amino acid. As used herein, a "corresponding non-natural amino acid" refers to a non-natural amino acid that is a derivative of the reference natural amino acid. For instance, a natural amino acid is substituted by the corresponding β-amino acid. β-amino acids have their amino group bonded to the β carbon rather than the α carbon as in the natural amino acids. For instance, α-alanine is substituted by β-alanine, etc. Other examples of substitution of a natural amino acid by a non-natural amino acid that is a derivative of the natural amino acid are the following. Alanine is, for instance, substituted by beta-alanine, t-butylalanine, 2-napthylalanine, L-3-(2-naphthyl)alanine, and 2-aminoisobutyric acid. Arginine is, for instance, substituted by homoarginine, ornithine, N5-carbamoylornithine, and 3-amino-propionic acid. Asparagine is, for instance, substituted by N-ethylasparagine. Aspartic acid is, for instance, substituted by 4-tert-butyl hydrogen 2-azidosuccinate. Cysteine is, for instance, substituted by cysteic acid and homocysteine. Glutamic acid is, for instance, substituted by γ-carboxy-DL-glutamic acid and 4-fluoro-DL-glutamic acid. Glutamine is, for instance, substituted by D-citrulline and thio-L-citrulline. Glycine is, for instance, substituted by N-methylglycine, t-butylglycine, N-methylglycine, and D-allylglycine. Histidine is, for instance, substituted by 3-(3-methyl-4-nitrobenzyl)-L-histidine methyl ester. Isoleucine is, for instance, substituted by isodesmosine, N-methylisoleucine, and allo-isoleucine. Leucine is, for instance, substituted by norleucine, desmosine, and 5,5,5-trifluoro-leucine. Lysine is, for instance, substituted by 6-N-methyllysine, 2-aminoheptanoic acid, N-acetyl lysine, hydroxylysine, and allo-hydroxylysine. Methionine is, for instance, substituted by methionin sulfoxide. Phenylalanine is, for instance, substituted by p-amino-L-phenylalanine, 3-benzothienyl alanine p-bromophenylalanine, p-acyl-L-phenylalanine, 2-fluorophenylalanine, 3-fluorophenylalanine, and 4-fluorophenylalanine. Proline is, for instance, substituted by 3-hydroxyproline, 4-hydroxyproline, and 1-acetyl-4-hydroxy-L-proline. Serine is, for instance, substituted by homoserine, isoserine, 3-phenylserine. Threonine is, for instance, substituted by D-thyroxine and allo-threonine. Tryptophan is, for instance, substituted by 5-hydroxy-tryptophan, 5-methoxy-tryptophan, and 5-fluoro-tryptophan. Tyrosine is, for instance, substituted by O-methyl-L-tyrosine, O-4-allyl-L-tyrosine, and 3-chloro-tyrosine. Valine is, for instance, substituted by norvaline, N-methylvaline, and 3-fluoro-valine.

A particularly preferred polypeptide according to the disclosure comprises amino acid sequence LAREYK-KIVEKLKRWLRQVLRTLR (SEQ ID NO:1) or a variant thereof having a lethal concentration (LC) of 99.9 in PBS of, at most, 3.2 μm selected from Tables 2, 3, 5 or 6. In one embodiment, a polypeptide having an LC of 99.9 in PBS of, at most, 2.4 μm selected from Tables 2, 3, 5 or 6 is provided.

A polypeptide according to the disclosure may consist of amino acid sequence LAREYKKIVEKLKRWLRQVLRTLR (SEQ ID NO:1) or a variant of this sequence as defined herein. As used herein, a "polypeptide" refers to peptides, polypeptides and peptidomimetics that comprise multiple amino acids. The terms "polypeptide" and "peptide" are used interchangeably. The smallest polypeptide according to the disclosure demonstrated to have antimicrobial activity has a length of 16 amino acids. However, the amino acid sequence or variant thereof can be part of a larger polypeptide, i.e., of a polypeptide that has been N-terminally and/or C-terminally extended by one or more additional amino acids. The amino acid sequence or variant of a polypeptide of the disclosure may be N-terminally and/or C-terminally modified, preferably by comprising an N- and/or C-terminal elongating group. Alternatively, the amino acid sequence or a variant thereof is N- and/or C-terminally extended. A polypeptide according to the disclosure, therefore, comprises at least 16 amino acids, and may comprise up to 1000 amino acids. However, smaller polypeptides are preferred in order to keep production costs as low as possible. Preferably, a polypeptide according to the disclosure is 16 to 200 amino acids in length, more preferably 16 to 100 amino acids, more preferably 16 to 50 amino acids. In one embodiment, a polypeptide according to the disclosure comprises 16 to 24 amino acids, i.e., 16, 17, 18, 19, 20, 21, 22, 23 or 24 amino acids. The polypeptide preferably has 16 to 24 amino acids. Such polypeptide having 16 to 24 amino acids may further have an N-terminal and/or C-terminal modification, such as an N-terminal modification selected from the group consisting of an acetyl-, hexanoyl-, decanoyl-, myristoyl-, NH—(CH$_2$—CH$_2$—O)$_{11}$—CO— and propionyl residue such as a C-terminal modification selected from the group consisting of amide-, NH—(CH$_2$—CH$_2$—O)$_{11}$—CO-amide- and one or two amino-hexanoyl groups. Examples of polypeptides with different lengths and their antimicrobial activity are provided in the Examples. In one embodiment, a polypeptide of the disclosure consists of amino acid sequence LAREYK-KIVEKLKRWLRQVLRTLR (SEQ ID NO:1) or a variant thereof as defined herein, optionally having an N-terminal and/or C-terminal modification, preferably comprising an N- and/or C-terminal elongating group.

As used herein, "peptidomimetic" refers to a compound containing non-peptidic structural elements, which compound mimics the antimicrobial, antibacterial, antiviral, antifungal, antiparasitic and/or anti-inflammatory properties of a polypeptide of the disclosure. Hence, a polypeptide of the disclosure may comprise non-peptidic structural elements. Such non-peptidic structural elements may be present in the amino acid sequence LAREYKKIVEKLKRWLRQV-LRTLR (SEQ ID NO:1), or in a variant thereof as defined herein, as a result of substitution of modification of one or more amino acids of the sequence or variant. Alternatively, a polypeptide of the disclosure may comprise non-peptidic structural elements outside the amino acid sequence LAR-EYKKIVEKLKRWLRQVLRTLR (SEQ ID NO:1), or in a variant thereof as defined herein, i.e., in the optional N- and/or C-terminal elongating groups. A non-peptidic structural element in a peptidomimetic is typically a modification of one or more existing amino acids. Preferred peptidomimetics are obtained by structural modification of polypeptides of the disclosure, for instance, using unnatural amino acids such as defined hereinabove, conformational restraints, cyclization of the polypeptide, isosteric replacement or other modifications. The amino acid sequence of a polypeptide according to the disclosure thus optionally comprises one or more modifications. Such polypeptide may be modified by natural processes, such as post-translational processing, or by chemical modification techniques. Modifications may be inserted at any location in the polypeptide, including in the polypeptide backbone, amino acid side-chains and at the N- or C-terminus. A single polypeptide may contain multiple types of modifications or several modification of a single type. Modifications include acetylation, amidation, acylation, phosphorylation, methylation, demethylation, ADP-ribosylation, disulfide bond formation, ubiquitination, gamma-carboxylation, glycosylation, hydroxylation, iodination, oxidation, pegylation and sulfation. In addition, a polypeptide according to the disclosure may be provided with a label, such as biotin, fluorescein or flavin, a lipid or lipid derivative, a sugar group. A polypeptide according to the disclosure can further be provided with a targeting moiety.

In a preferred embodiment, a polypeptide, according to the disclosure wherein the amino acid sequence LAREYK-KIVEKLKRWLRQVLRTLR (SEQ ID NO:1) or the variant thereof, as defined herein, is N-terminally and/or C-terminally modified. A polypeptide of the disclosure thus preferably comprises an N- and/or C-terminal elongating group. N- and C-terminal elongating groups that can be used in a polypeptide of the disclosure are well known in the art. Preferred examples of an N-terminal modification are an acetyl-, a hexanoyl-, a decanoyl-, a myristoyl-, a NH—(CH$_2$—CH$_2$—O)$_{11}$—CO— and a propionyl residue. Preferred examples of a C-terminal modification are an amide-, a NH—(CH$_2$—CH$_2$—O)$_{11}$—CO-amide-, and one or two amino-hexanoyl groups. However, other N- or C-terminal elongating groups will also yield active compounds that are known to a person skilled in the art. In one embodiment, the amino acid sequence LAREYKKIVEKLKRWLRQVL-RTLR (SEQ ID NO:1) or the variant thereof as defined herein comprises an N-terminal acetyl-, hexanoyl-, decanoyl-, myristoyl-, NH—(CH$_2$—CH$_2$—O)$_{11}$—CO— or propionyl residue and a C-terminal amide-, NH—(CH$_2$—CH$_2$—O)$_{11}$—CO-amide-, and one or two amino-hexanoyl groups. As demonstrated in the Examples (Table 3), polypeptides having such N-terminal or C-terminal modifications retain the high antimicrobial activity. In one embodiment, a polypeptide according to the disclosure is provided wherein the N-terminus is acetylated and the C-terminus is amidated.

The disclosure thus provides an isolated or recombinant polypeptide comprising an amino acid sequence LAREYK-KIVEKLKRWLRQVLRTLR (SEQ ID NO:1), or a variant of the amino acid sequence, the polypeptide having antimicrobial, antibacterial, antiviral, antifungal, antiparasitic and/or anti-inflammatory activity, the variant having at least 16 amino acids and having up to 5, preferably up to 3, more preferably up to 1 of the following amino acid substitutions:

substitution of L at amino acid position 1 by I, V or A
substitution of A at amino acid position 2 by L, V, Q or I
substitution of R at amino acid position 3 by K or H
substitution of E at amino acid position 4 by Q
substitution of Y at amino acid position 5 by F or W
substitution of K at amino acid position 6 by R or H
substitution of K at amino acid position 7 by R or H
substitution of I at amino acid position 8 by L, V or A
substitution of V at amino acid position 9 by L, I or A
substitution of E at amino acid position 10 by Q
substitution of K at amino acid position 11 by R or H
substitution of L at amino acid position 12 by I, V or A
substitution of K at amino acid position 13 by R or H
substitution of R at amino acid position 14 by K or H
substitution of W at amino acid position 15 by F or Y
substitution of R at amino acid position 17 by H or K
substitution of Q at amino acid position 18 by N, A, S or T
substitution of V at amino acid position 19 by L, I or A
substitution of L at amino acid position 20 by I, V or A
substitution of R at amino acid position 21 by K or H
substitution of T at amino acid position 22 by Q, N or A
substitution of R at amino acid position 24 by H or K
substitution of 1 to 4 amino acids by a corresponding D-amino acid, wherein the amino acid sequence or the variant thereof comprises an N- and/or C-terminal elongating group, preferably comprising an N-terminal acetyl-, hexanoyl-, decanoyl-, myristoyl-, NH—(CH$_2$—CH$_2$—O)$_{11}$—CO— or propionyl residue and a C-terminal amide-, NH—(CH$_2$—CH$_2$—O)$_{11}$—CO-amide-, and one or two amino-hexanoyl groups. It will be clear to a person skilled in the art that other N- or C-terminal elongating groups will also yield active compounds. Herein, the numbering of amino acids is as follows:

L$_1$A$_2$R$_3$E$_4$Y$_5$K$_6$K$_7$I$_8$V$_9$E$_{10}$K$_{11}$L$_{12}$K$_{13}$-R$_{14}$W$_{15}$L$^{16}$R$_{17}$Q$_{18}$V$_{19}$L$_{20}$R$_{21}$T$_{22}$L$_{23}$R$_{24}$. The polypeptide preferably has 16 to 24 amino acids.

In a preferred embodiment, a polypeptide according to the disclosure comprises a hydrophobic moiety. Addition of hydrophobic groups to cationic (poly)peptides improves their ability to neutralize microbial endotoxin and to interact with microbial membranes and thus improves their ability to eliminate microbes, e.g., pathogens.

As described herein above, a polypeptide according to the disclosure may be modified by chemical modification techniques known in the art. The modifications of the polypeptides according to the disclosure can be introduced during or at the end of synthesis of the polypeptide. For instance, when the polypeptide is synthesized using solid-phase synthesis technique, N-terminal acetylation can be performed at the end by reacting the amino acid sequence, which is still bound to the resin, with acetic acid. As another example, C-terminal amidation, is, for instance, performed using a special kind of resin in solid-phase peptide synthesis, such as the commercially available Tentagel S AM (ex Rapp, Tubingen, Germany). These resins comprise a chemical handle from which amidated (poly)peptides are released during the cleavage. These and other methods of modifying polypeptides are known to any person skilled in the art.

In one embodiment, the disclosure provides an isolated or recombinant polypeptide comprising an amino acid sequence LAREYKKIVEKLKRWLRQVLRTLR (SEQ ID NO:1), or a variant of the amino acid sequence, the polypeptide having antimicrobial, antibacterial, antiviral, antifungal, antiparasitic and/or anti-inflammatory activity, the variant having at least 16 amino acids and:
having up to 5 of the following amino acid substitutions:
substitution of one or more amino acids selected from the group of L, I, V or A by another amino acid selected from the group;
substitution of one or more amino acids selected from the group of R, K or H by another amino acid selected from the group;
substitution of E by Q
substitution of Y or W by F
substitution of one or more amino acids selected from the group of Q, N, A, S or T by another amino acid selected from the group, and/or
having one or more substitutions of an amino acid by a corresponding D-amino acid.

The disclosure further provides a multimer comprising up to six polypeptides comprising amino acid sequence LAREYKKIVEKLKRQVLRTLR (SEQ ID NO:1) or a variant thereof as defined herein. The multimer may comprise up to six polypeptide monomers having the same amino acid sequence or up to six polypeptide monomers whereby two or more polypeptide monomer have a different amino acid sequence. In a preferred embodiment, a multimer according to the disclosure comprises up to six polypeptides according to the disclosure having the same amino acid sequence.

Salts of polypeptides according to the disclosure are also provided. Such salts include, but are not limited to, acid addition salts and base addition salts. As used herein, "pharmaceutically acceptable salt" of a polypeptide refers to a salt that retains the desired antimicrobial, antibacterial, antifungal, antiviral, antiparasitic and/or anti-inflammatory activity of the polypeptide, and is suitable for administration to humans or animals. Methods for the preparation of salts of polypeptides are known in the art and generally involve mixing of the polypeptide with a pharmaceutically acceptable acid or base, for instance, by reacting the free acid or free base forms of the product with one or more equivalents of the appropriate acid or base in a solvent or medium in which the salt is insoluble, or in a solvent such as water, which is then removed in vacuo or by freeze-drying, or by exchanging the cations of an existing salt for another cation on a suitable ion exchange resin. Examples of pharmaceutically acceptable acids and bases include organic and inorganic acids such as formic acid, acetic acid, propionic acid, lactic acid, glycolic acid, oxalic acid, pyruvic acid, succinic acid, maleic acid, malonic acid, trifluoroacetic acid, cinnamic acid, sulfuric acid, hydrochloric acid, hydrobromic acid, nitric acid, perchloric acid, phosphoric acid, and thiocyanic acid, which form ammonium salts with free amino groups of polypeptides, and bases that form carboxylate salts with free carboxylic groups of polypeptides, such as ethylamine, methylamine, dimethylamine, triethylamine, isopropylamine, diisopropylamine, and other mono-, di-and trialkylamines, and arylamines.

Polypeptides according to the disclosure can be prepared by various methods. For instance, a polypeptide can be synthesized by commonly used solid-phase synthesis methods, e.g., methods that involve t-BOC or FMOC protection of alpha-amino groups that are well known in the art. Here, amino acids are sequentially added to a growing chain of amino acids. Such methods are, for instance, described in Merrifield (1963), *J. Am. Chem. Soc.* 85:2149-2156; and Atherton et al., "Solid Phase Peptide Synthesis," IRL Press, London, (1989). Solid-phase synthesis methods are particularly suitable for synthesis of polypeptides or relatively short length, such as polypeptides with a length of up to about 70 amino acids in large-scale production.

Alternatively, a polypeptide of the disclosure can be prepared using recombinant techniques well known in the art in which a nucleotide sequence encoding the polypeptide is expressed in host cells. The disclosure thus provides a method for the preparation of a polypeptide according to the disclosure comprising:
providing a nucleic acid molecule comprising a nucleic acid sequence encoding a polypeptide according to the disclosure;
transforming a host cell with the nucleic acid molecule;
culturing the host cell under conditions that allow expression of the polypeptide;
harvesting the polypeptide from the cells;
optionally N-terminally or C-terminally modifying the polypeptide, for instance, by addition of an N- and/or C-terminal elongating group.

The disclosure further provides a nucleic acid molecule comprising a nucleic acid sequence encoding a polypeptide according to the disclosure, which is herein also referred to as a nucleic acid molecule according to the disclosure. As used herein, a nucleic acid molecule or nucleic acid sequence of the disclosure comprises a chain of nucleotides, preferably DNA and/or RNA.

Further provided is a vector comprising a nucleic acid sequence molecule according to the disclosure. The term "vector" as used herein refers to a nucleic acid molecule, such as a plasmid, bacteriophage or animal virus, capable of introducing a heterologous nucleic acid sequence into a host cell. A vector according to the disclosure allows the expression or production of a polypeptide of the disclosure encoded by the heterologous nucleic acid sequence in a host cell. A vector used in accordance with the disclosure is, for instance, derived from an animal virus, examples of which include, but not limited to, vaccinia virus (including attenuated derivatives such as the Modified Vaccinia virus Ankara, MVA), Newcastle Disease virus (NDV), adenovirus or retrovirus. A vector according to the disclosure preferably comprises an expression cassette comprising a promoter that is suitable for initiation of transcription of a polypeptide according to the disclosure in the selected host cells. Examples of suitable promoters for expression of polypeptides according to the disclosure in eukaryotic host cells include, but are not limited to, beta-actin promoter, immunoglobin promoter, 5S RNA promoter, or virus-derived promoters such as cytomegalovirus (CMV), Rous sarcoma virus (RSV) and Simian virus 40 (SV40) promoters for mammalian hosts.

Further provided by the disclosure is a recombinant host cell comprising a nucleic acid molecule and/or a vector according to the disclosure. A host cell is a cell that has been transformed, or is capable of transformation, by a nucleic acid molecule such as a vector according to the disclosure. "Transformation" refers to the introduction of a foreign nucleic acid into a recipient cell. Transformation of a host cell can result in transient expression of a recombinant protein by the cell, meaning that the recombinant protein is only expressed for a defined period of time. Alternatively, transformation of a recipient cell can result in stable expression, meaning that the nucleic acid is introduced into the genome of the cell and thus passed on to the next generations of cells. Additionally, inducible expression of a recombinant protein can be achieved. An inducible expression system requires the presence or absence of a molecule that allows for expression of a nucleic acid sequence encoding a polypeptide of the disclosure. Examples of inducible expression systems include, but are not limited to, Tet-On and Tet-Off expression systems, hormone-inducible gene expression system such as, for instance, an ecdysone-inducible gene expression system, an arabinose-inducible gene expression system, and a Drosophila-inducible expression system using a pMT/BiP vector (INVITROGEN®), which comprises an inducible metallothioneine promoter. A host cell used in a method for the preparation of a polypeptide according to the disclosure is, for instance, a gram-positive prokaryote, a gram-negative prokaryote or a eukaryote. Preferably, the host cell is a eukaryotic cell, such as a plant cell, a yeast cell, a mammalian cell or an insect cell, most preferably an insect cell or a mammalian cell. Examples of suitable host cells include plant cells such as corn cells, rice cells, duckweed cells, tobacco cells (such as BY-2 or NT-1 cells), and potato cells. Examples of yeast cells are *Saccharomyces* and *Pichia*. Examples of insect cells are *Spodoptera frugiperda* cells, such as Tn5, SF-9 and SF-21 cells, and Drosophila cells, such as *Drosophila* Schneider 2 (S2) cells. Examples of mammalian cells that are suitable for expressing a polypeptide according to the disclosure include, but are not limited to, African Green Monkey kidney (Vero) cells, baby hamster kidney (such as BHK-21) cells, Human retina cells (for example PER.C6® cells), human embryonic kidney cells (such as HEK293 cells), Madin Darby Canine kidney (MDCK) cells, Chicken embryo fibroblasts (CEF), Chicken embryo kidney cells (CEK cells), blastoderm-derived embryonic stem cells (e.g., EB14), mouse embryonic fibroblasts (such as 3T3 cells), Chinese hamster ovary (CHO) cells, and derivatives of these cell types.

A method according to the disclosure preferably further comprises a step of harvesting, purifying and/or isolating polypeptides according to the disclosure. Obtained polypeptides according to the disclosure are preferably used in human therapy, optionally after additional purifying, isolation or processing steps, for instance, purification using gel electrophoresis or chromatography methods.

A polypeptide according to the disclosure exhibits a number of activities that can be advantageously used in both therapeutic and nontherapeutic applications. In particular, polypeptides according to the disclosure are useful in counteracting various microbial infections, such as bacterial infections, fungal infections, viral infections, and in counteracting parasitic infections. Provided, thus, are pharmaceutical compositions comprising a polypeptide according to the disclosure or a pharmaceutically acceptable salt thereof, and at least one pharmaceutically acceptable carrier, diluent and/or excipient. Also provided are pharmaceutical compositions comprising a nucleic acid molecule or vector according to the disclosure and at least one pharmaceutically acceptable carrier, diluent and/or excipient.

The disclosure further provides a polypeptide according to the disclosure for use as a medicament. Further provided is a nucleic acid molecule comprising a nucleic acid sequence encoding a polypeptide according to the disclosure for use as a medicament. The medicament can be a therapeutic or a prophylactic agent.

In one embodiment, the disclosure provides a method for the treatment of a subject suffering from bacterial, fungal, viral and/or parasitic infection comprising administering to the subject a therapeutically effective amount of a polypeptide according to the disclosure, a pharmaceutical composition according to the disclosure, or a nucleic acid molecule according to the disclosure. Also provided is a method for the preparation of a medicament for the treatment of a subject infected with a microbe or for prophylaxis of a microbial infection. In a preferred embodiment, the microbe is a bacterium, a fungus, a virus or a parasite. Further provided is a polypeptide and/or nucleic acid molecule for use according to the disclosure in the treatment of a microbial, bacterial, fungal, viral and/or parasitic infection or a condition resulting from a microbial, bacterial, fungal, viral and/or parasitic infection.

As used herein, a "subject" is a human or an animal. Subjects include, but are not limited to, mammals such as humans, pigs, ferrets, seals, rabbits, cats, dogs, cows and horses, and birds such as chickens, ducks, geese and turkeys. In a preferred embodiment of the disclosure, a subject is a mammal. In a particularly preferred embodiment, the subject is a human.

The disclosure also provides a method for inhibiting the growth of a microbe, e.g., a bacterium, a virus, a fungus, or a parasite comprising contacting the microbe or parasite with a polypeptide or pharmaceutical composition according to the disclosure. The contacting can be performed in vivo and in vitro.

The polypeptides and pharmaceutical compositions according to the disclosure are effective in treating a variety of microbial infections, such as various viral, bacterial and fungal infections. For example, the polypeptides and pharmaceutical compositions are effective in treating gram-negative and gram-positive bacteria. Examples of pathogenic bacteria that may cause infections in humans or animals that are treatable with polypeptides and compositions of the disclosure include, but are not limited to, *Listeria, Escherichia, chlamydia, rickettsial bacteria, mycobacteria, staphylococci, streptococci, pneumonococci,*

*meningococci, Klebsiella, pseudomonas, Legionella, diphtheria, salmonella, bacilli, Vibrio cholerae, tetanus, Clostridium, Bacillus, Yersinia*, and *Leptospira* bacteria.

Examples of pathogenic viruses that may cause infections in humans or animals that are treatable with polypeptides and compositions of the disclosure include, but are not limited to, A, B or C hepatitis, herpes virus (for instance, VZV, HSV-I, HAV-6, HSV-II, CMV, EpsteinBarr-virus), adenovirus, influenza virus, flaviviruses, echovirus, rhinovirus, Coxsackie virus. coronavirus, respiratory syncytial virus (RSV), rotavirus, Morbillivirus, rubella virus, parvovirus, vaccinia virus, HTLV virus, dengue virus, papillomavirus, poliovirus, rabies virus and human immunodeficiency virus (HIV virus e.g., type I and II).

Examples of pathogenic fungi that may cause infections in humans or animals that are treatable with polypeptides and compositions of the disclosure include, but are not limited to, *Candida* (e.g., *albicans, krusei, glabrata, tropicalis*), *Aspergillus* (e.g., *fumigatus, niger*), *Cryptococcus neoformans, Histoplasma capsulatum*, Genus *Mucorales, Blastomyces dermatitidis, Paracoccidioides brasiliensis*, and *Coccidioides immitis*.

Examples of pathogenic parasites that may cause infections in humans or animals that are treatable with polypeptides and compositions of the disclosure include, but are not limited to, *Entamoeba histolytica, Plasmodium* (e.g., *falciparum, vivax*), *Entamoeba, Giardia, Balantidium coli, Acanthamoeba, Cryptosporidium* sp., *Pneumocystis carinii, Babesia microti, Trypanosoma* (e.g., *brucei, cruzi*), *Leishmania* (e.g., *donovani*), and *Toxoplasma gondii*.

In a preferred embodiment, polypeptides and pharmaceutical compositions of the disclosure are effective in treating infections caused by methicillin-resistant *Staphylococcus aureus* (MRSA) and (non-resistant) *S. aureus*, the gram-negative bacterium *Pseudomonas aeruginosa* and the fungal species *Candida albicans* and *Aspergillus niger.*

The compositions containing the polypeptides can be administered for prophylactic and/or therapeutic treatments. In therapeutic applications, polypeptides or compositions are administered to a subject, preferably a human, already suffering from a disease in an amount sufficient to counteract the symptoms of the infection or the condition resulting from the infection and its complications. In prophylactic applications, polypeptides or compositions are administered to a subject, for instance, a human or animal at risk of suffering from a microbial or parasitic infection in an amount sufficient to prevent infection or at least inhibit the development of an infection. The polypeptide is typically present in a pharmaceutical composition according to the disclosure in a therapeutic amount, which is an amount sufficient to remedy a condition or disease, particularly symptoms associated with a microbial or parasitic infection. Typical doses of administration of a polypeptide according to the disclosure or combinations of at least two thereof are between 0.01 and 10 mg polypeptide per kg body weight, depending on the size of the polypeptide.

Polypeptides and pharmaceutical composition of the disclosure are particularly suitable for topical application, e.g., in the treatment or prevention of skin infections, wound infections and urinary tract infections. As detailed herein before, polypeptides of the disclosure are capable of preventing biofilm formation and disperse existing biofilms, kill the bacteria, fungi or other microbes at and around the site of biofilm formation, and modulate immune responses by neutralizing pro-inflammatory microbial endotoxins. Bacterial biofilms may delay cutaneous wound healing and reduce topical antibacterial efficiency of conventional antibiotics in healing or treating infected skin wounds, skin infections or urinary tract infections. Polypeptides according to the disclosure are, for instance, particularly useful in wound healing as demonstrated in the Examples of the present application. The Examples show that polypeptides of the disclosure are effective in killing bacteria residing in biofilms in a burn wound infection model of human fibroblasts. In one embodiment, the disclosure, therefore, provides a polypeptide, pharmaceutical composition and/or nucleic acid molecule according to the disclosure for use in the treatment or prevention of skin infection, wound infection and/or urinary tract infections. Also provided is the use of a polypeptide, pharmaceutical composition and/or nucleic acid molecule according to the disclosure for use in wound healing. Further provided is the use of a polypeptide, pharmaceutical composition and/or nucleic acid molecule according to the disclosure in the manufacture of a pharmaceutical composition for the treatment or prevention of skin infection, wound infection, urinary tract infection and/or for wound healing. The disclosure further provides a method for the treatment of a subject suffering from skin infection, wound infection and/or urinary tract infection comprising administering to the subject a therapeutically effective amount of a polypeptide according to the disclosure, a pharmaceutical composition according to the disclosure, or a nucleic acid molecule according to the disclosure.

The polypeptides and pharmaceutical compositions are also useful as anti-inflammatory agents as they neutralize pro-inflammatory microbial endotoxins such as lipoteichoic acid, peptidoglycan and lipopolysaccharides, thereby inhibiting, reducing or preventing influx of neutrophils, macrophages/monocytes and lymphocytes and the release of pro-inflammatory microbial compounds by the infected subject. Also provided is, therefore, a method for inhibiting the release of pro-inflammatory compounds comprising contacting a cell capable of releasing pro-inflammatory compounds with a polypeptide according to the disclosure. The contacting can be performed in vivo and in vitro. Further provided is a polypeptide according to the disclosure for use as an anti-inflammatory agent.

A polypeptide of the disclosure is advantageously incorporated in a controlled release and/or targeted delivery carrier. As used herein, the term "controlled release" refers to the release of the polypeptide of the disclosure in a time-dependent manner. In one embodiment, controlled release refers to slow release. As used herein, the term "targeted delivery" refers to the release of the polypeptide of the disclosure in a site-directed manner. Use of a controlled release vehicle has the advantage that frequent administration such as by injection of the polypeptide of the disclosure can be avoided. Use of a targeted delivery vehicle has the advantage that the polypeptide of the disclosure is effectively delivered to and/or retained at a site of interest in a subject's body, such as a site of inflammation or a site of infection. Preferably, a polypeptide of the disclosure is targeted to a site infected by microorganisms including bacteria, fungi, viruses and parasites. Controlled release and/or targeted delivery carriers are well known in the art. Non limiting examples of controlled release and/or targeted delivery vehicles are nanoparticles, microparticles, nanocapsules, microcapsules, liposomes, microspheres, hydrogels, polymers, lipid complexes, serum albumin, antibodies, cyclodextrins and dextrans. Controlled release is, for instance, provided by incorporating a polypeptide of the disclosure in or on the surface of such carrier. The carriers are of materials that form particles that capture a polypeptide of the disclosure and slowly degrade or dissolve in a suitable environment, such as aqueous, acidic or basic environment or body fluids, and thereby release the polypeptide. Targeted delivery is, for instance, achieved by providing a carrier with targeting groups on the surface thereof Examples of such carrier comprising targeting groups are antibody-functionalized carriers, carriers having a site-specific ligand and carriers having a positive or negative surface charge. Preferred particles for controlled release and/or targeted delivery are nanoparticles, i.e., particles in the range of about 1 to 500 nm in diameter, preferably up to about 200 nm in diameter, and liposomes, optionally provided with targeting groups.

The disclosure, therefore, further provides a controlled release carrier comprising a polypeptide of the disclosure and pharmaceutical compositions comprising such controlled release carrier. Also provided are a targeted delivery carrier comprising a polypeptide of the disclosure, and pharmaceutical compositions comprising such targeted delivery carrier. The carrier is in one embodiment selected from the group consisting of nanoparticles, microparticles, nanocapsules, microcapsules, liposomes, microspheres, hydrogels, polymers, lipid complexes, serum albumin, antibodies, cyclodextrins and dextran.

Preferred targeted delivery and/or controlled release carriers are of biodegradable material. "Biodegradable" as used herein refers to molecules that degrade under physiological conditions. This includes molecules that are hydrolytically degradable and molecules that require enzymatic degradation. Suitable biodegradable materials include, but are not limited to, biodegradable polymers and natural biodegradable material such as PLA (polylactic acid), PGA (polyglycolic acid), polycaprolactone (PCA), polyethylene oxide (PEO), polydioxanone (PDS), polycaprolactone (PCL), polypropylene fumarate, polymers derived from lactones, such as lactide, glycolide and caprolactone, carbonates such as trimethylene carbonate and tetramethylene carbonate, dioxanones, ethylene glycol, polyester amide (PEA) ethylene oxide, esteramides, γ-hydroxyvalerate, β-hydroxypropionate, α-hydroxy acid, hydroxybuterates, hydroxy alkanoates, polyimide carbonates, polyurethanes, polyanhydrides, and combinations thereof, polysaccharides such as hyaluronic acid, chitosan and cellulose, and proteins such as gelatin and collagen.

Polypeptides of the disclosure can be further advantageously used as a preservative for materials that are susceptible to microbial, e.g., bacterial, viral, fungal, or parasitic infections. Such material can be impregnated or coated with or covered by a polypeptide of the disclosure. In one embodiment, a polypeptide of the disclosure is used as a preservative for medical devices. The term "medical devices" as used herein refers to devices that can be used in the human or animal body and includes, but is not limited to, medical instruments, medical implements, prostheses, such as artificial joints including hips and knees, and dental prostheses, breast implants, implantable devices such as pace makers, heart valves, stents, catheters, ear tubes, splints, screws for medical devices, and wound or tissue dressings. Such medical devices are particularly suitable for adherence by, for instance, bacteria, both for adherence of individual bacteria and for bacteria in biofilms.

Also provided is, therefore, the use of a polypeptide of the disclosure as a preservative for medical devices. Further provided is a coating, preferably for medical devices, comprising a polypeptide of the disclosure. In one embodiment, such coating provides for controlled release of the polypeptide of the disclosure. Such controlled release coating for medical devices preferably comprises a biodegradable material so that release of the polypeptide of the disclosure is achieved by degradation of the coating material. Also provided is, therefore, a controlled release coating comprising a polypeptide of the disclosure. Further provided is a medical device comprising such coating comprising a polypeptide of the disclosure and a biodegradable material. A biodegradable coating in accordance with the disclosure comprises a biodegradable material as defined above. In particular, such biodegradable coating comprises a material selected from the group consisting of PLA (polylactic acid), PGA (polyglycolic acid), polycaprolactone (PCA), polyethylene oxide (PEO), polydioxanone (PDS), polycaprolactone (PCL), polypropylene fumarate, polymers derived from lactones, such as lactide, glycolide and caprolactone, carbonates such as trimethylene carbonate and tetramethylene carbonate, dioxanones, ethylene glycol, polyester amide (PEA) ethylene oxide, esteramides, γ-hydroxyvalerate, β-hydroxypropionate, α-hydroxy acid, hydroxybuterates, hydroxy alkanoates, polyimide carbonates, polyurethanes, polyanhydrides, and combinations thereof, polysaccharides such as hyaluronic acid, chitosan and cellulose, and proteins such as gelatin and collagen.

Although polypeptides according to the disclosure are potent antimicrobial agents, they can be combined with known antimicrobial agents, such as conventional anti-infectives, such as antibiotics, antivirals and antifungals or other antimicrobial peptides, and antibodies and chemicals, e.g., sensitizers and nano-particles. Such combination may result in an increased antimicrobial activity or broaden the spectrum of activity. Polypeptides of the disclosure may, for instance, be combined with penicillins, cephalosporins, macrolides, fluoroquinolones, sulfonamides, tetracylcines and/or aminoglycosides for treating bacterial infections. For treatment of viral infections, polypeptides may be combined with antiviral nucleoside analogs such as aciclovir, ganciclovir, zidovudine (AZT) or didanosine or neuramidase inhibitors such as oseltamivir, peramivir or zanamivir. For treatment of fungal infections, the polypeptides and compositions of the disclosure may be combined with polyene antifungals, imidazoles, triazoles, allylamines, echinocandins, ciclopirox, flucytosine and/or griseofulvin. The disclosure, therefore, provides a pharmaceutical composition comprising a polypeptide according to the disclosure and an additional antimicrobial agent, such as an antibiotic or an antimicrobial peptide, preferably selected from the group consisting of penicillins, cephalosporins, carbapenems, and mupirocin.

Pharmaceutical compositions according to the disclosure comprise at least one pharmaceutically acceptable carrier, diluent or excipient. Examples of suitable carriers, for instance, comprise keyhole limpet haemocyanin (KLH), serum albumin (e.g. BSA or RSA) and ovalbumin. In a preferred embodiment, the suitable carrier is a solution, for example, saline. Examples of excipients that can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; and a flavoring agent such as peppermint, oil of wintergreen or cherry. When the dosage unit form is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor. A pharmaceutical composition according to the disclosure is preferably suitable for human use.

The pharmaceutical compositions described herein can be administered in a variety of different ways. Examples include administering a pharmaceutical composition comprising a polypeptide according to the disclosure and containing a pharmaceutically acceptable carrier via oral, intranasal, rectal, topical, intraperitoneal, intravenous, intramuscular, subcutaneous, subdermal, transdermal, intrathecal, and intracranial methods. For oral administration, the active ingredient can be administered in solid dosage forms, such as capsules, tablets, and powders, or in liquid dosage forms, such as elixirs, syrups, and suspensions.

Sterile compositions for injection can be formulated according to conventional pharmaceutical practice by dissolving or suspending the polypeptide of the disclosure in a vehicle for injection, such as water or a naturally occurring vegetable oil like sesame oil, coconut oil, peanut oil, cottonseed oil, etc., or a synthetic fatty vehicle like ethyl oleate or the like. Buffers, preservatives, antioxidants and the like may also be incorporated.

In a preferred embodiment, a pharmaceutical composition according to the disclosure is formulated for topical administration. "Topical administration" as used herein refers to application to a body surface such as the skin or mucous membranes to locally treat conditions resulting from microbial or parasitic infections. Examples of formulation suitable for topical administration include, but are not limited to, a cream, gel, ointment, lotion, foam, suspension, spray, aerosol, or powder aerosol. Topical medicaments can be epicutaneous, meaning that they are applied directly to the skin. Topical medicaments can also be inhalational, for instance, for application to the mucosal epithelium of the respiratory tract, or applied to the surface of tissues other than the skin, such as eye drops applied to the conjunctiva, or ear drops placed in the ear. The pharmaceutical composition formulated for topical administration preferably comprises at least one pharmaceutical excipient suitable for topical application, such as an emulgent, a diluent, a humectant, a preservative, a pH adjuster and/or water.

A polypeptide according to the disclosure is also particularly suitable for diagnostic use. The polypeptides may be used for the detection of microbial infection, for instance, by the detection of microbial toxins, e.g., bacterial toxins including LPS, LTA and PG, present in physiological samples, such as blood, plasma, mucus, wound exudate and urine. Further, the polypeptides can be used for determining the amount of microbial toxins in such samples. Provided is, therefore, a polypeptide nucleic acid molecule according to the disclosure for use as a diagnostic agent. Further provided is a use of a polypeptide according to the disclosure for detecting a microbial toxin, preferably a bacterial or fungal toxin, in a physiological sample, such as a blood, plasma, mucus, wound exudate and urine sample. As described above, a polypeptide according to the disclosure can be coupled to a suitable moiety such as a biotin, a fluorescein label, a near infrared dye or a radioactive isotope. Such labeled polypeptides can be used in a method for detecting microbial infections such as bacterial infections because they migrate to a site of microbial infection. Using a detector suitable for the used label attached to the polypeptide, it is possible to detect infection sites. Methods for detecting microbial infections such as bacterial infections are, therefore, also provided by the disclosure. The method typically involves administering a labeled polypeptide to a subject infected with, or suspected of being infected with, a microbial organism. Because the labeled polypeptide is capable of interacting with the infectious organism, it accumulates at the site of infection. For detecting microbial toxins in a physiological sample, the method involves administering a labeled polypeptide to a physiological sample of a subject infected with, or suspected of being infected with, a microbial organism. It is possible to detect the accumulation of the polypeptide at the site of infection or in a sample using various detectors that are sensitive to the label that is attached to the polypeptide.

Another useful application of polypeptides according to the disclosure is in preservation of food products. Also provided is, therefore, the use of a polypeptide according to the disclosure as a food preservative. Generally, pathogenic or spoilage microorganisms are destroyed by thermally processing foods by subjecting them to temperatures varying from 60° C. to 100° C. Such treatment may have undesirable effects on the food product, such as undesirable organoleptic effects. Use of a polypeptide according to the disclosure as a preservative in food products may result in extended storage life and/or enhanced safety of the food product.

Pathogenic microorganisms in foods may cause infections or intoxication of subjects, and include bacteria such as *Campylobacter jejuni, Salmonella typhi, Salmonella paratyphi* and non-*typhi Salmonella* species, *Staphylococcus aureus, Escherichia coli, Listeria monocytogenes, Shigella* and *Clostridium Botulinum*, viruses such as Rotaviruses and Norwalk virus, parasites such as *Taenia solium, Taenia saginata* and *Trichinella spiralis* and molds. Food spoilage refers to the change of look, consistency, flavor and/or odor of food products, and may be caused by bacteria such as *Lactobacillus, Leuconostoc, Pseudomonas, Micrococcus, Flavobacterium, Serratia, Enterobacter* and *Streptococcus*, and fungi such as *Aspergillus, Fusarium* and *Cladosporium* and yeasts.

The disclosure will be explained in more detail in the following, non-limiting examples.

BRIEF DESCRIPTION OF THE DRAWINGS

FIGS. 2A and 2B: Killing of MRSA LUH14616 by peptides P60.4Ac (M.J. Nell et al., *Peptides* (2006) 649-660) and peptides P2, P3, P4, P5, P6, P9, P10, P11, P12, P13, P14, P15, P16, P17 and P19, represented by the amount of CFU (colony-forming units) of MRSA per ml of culture medium by different concentrations of the peptides (FIG. 2A) and IC90, IC99 and IC99.9 (90%, 99% and 99.9% Inhibitory Concentration) values for the peptides (FIG. 2B).

DETAILED DESCRIPTION

Examples

Figure 1:
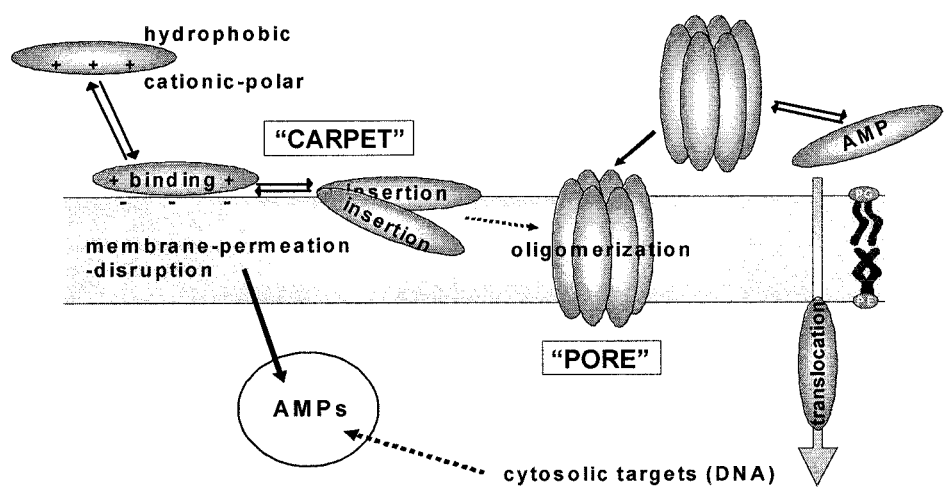
FIG. 1: Simplified scheme of steps involved in the mode of action of AMPs indicating the two most prominent models for membrane disruption (carpet and pore formation) and AMP transfer to the intracellular environment. In order to bind to the cytoplasmic bacterial membrane, predominantly composed of anionic phosphatidylglycerol (PG) and neutral phosphatidylethanolamine (PE), AMPs have to translocate through the extracellular biofilm polymer matrix as well as the outer membrane and/or peptidoglycan/lipoteichoic acid layer (not shown for simplicity), which is mostly electrostatically driven.

Materials and Methods
Synthesis of Antimicrobial Peptides

Synthetic peptides were prepared by normal Fmoc-chemistry using preloaded Tentagel resins, PyBop/NMM for in situ activation and 20% piperidine in NMP for Fmoc removal [H. S. Hiemstra et al., Proc. Natl. Acad. Sci. U.S.A. 94:10313-10318 (1997)]. Couplings were performed for 60 minutes with six-fold acylating species. After final Fmoc removal, peptides were cleaved with TFA/H$_2$O 19/1 (v/v) containing additional scavengers when C (triethylsilane) or W (ethanethiol) were present in the peptide sequence. Peptides were isolated by ether/pentane 1/1 (v/v) precipitation and isolation of the product by centrifugation. After air-drying at about 40° C., peptides were dissolved in acetic acid/water 1/10 (v/v) and lyophilized. Peptides were checked on purity using UPLC-MS (Acquity, Waters) and on integrity using Maldi-Tof mass spectrometry (Microflex, Bruker), showing the expected molecular masses.

Abbreviations:
Fmoc: 9H-fluorenylmethyloxycarbonyl
NMM: N-methylmorpholin
PyBOP: Benzotriazol-1-yl-oxy-tris-pyrrolidino-phosphonium hexafluorophosphate
TFA: trifluoro acetic acid Bacterial Strains The clinical isolate of methicillin-resistant *Staphylococcus aureus* (MRSA), LUH14616 was kindly provided by Dr. S. Croes, Maastricht University Medical Center, Maastricht, Netherlands (see S.B.M.C. Croes, Microbiol. 2009; 9:229. doi: 10.1186/1471-2180-9-229) and that of mupirocine-resistant MRSA LUH15051 was a gift from Dr. M.E.O.C. Heck (Laboratory for Infectious Diseases and Screening, National Institute for Public Health and Environment, RIVM, Bilthoven, Netherlands).

*S. aureus* JAR is described in Campoccia et al. (*Int. J. Artif. Organs,* 2008 September; 31(9):841-7).

Bacteria were stored at -80° C. until use. Inoculi of mid-log phase bacteria were prepared by incubating isolated MRSA colonies from blood agar plates in Tryptic Soy Broth (TSB) medium (Becton Dickinson, Le Pont de Clax, France) for 2.5 hours and then diluted to the concentration needed.

TABLE 1

| Strain ID | specie | Resistance | |
|---|---|---|---|
| LUH14616 | S. aureus | methicillin | Croes et al. 2009 |
| LUH15051 | S. aureus | Methicillin and mupirocine | RIVM |
| JAR | S. aureus | | Campoccia et al. 2008 |

In Vitro Killing Assay

For the in vitro killing assay on mid-log phase bacteria, MRSA LUH14616 and MRSA LUH15051 were resuspended to a concentration of 1×10$^6$ bacteria/ml in PBS. Subsequently, 200 μl was added to a concentration range of peptides LL-37, P60.4Ac (OP-145) and P10 that were lyophilized in advance. Subsequently, the bacteria-peptide mixture was incubated for 1 hour at 37° C. To establish the killing capacity of these peptides, the suspensions were serially diluted and plated onto DST agar plates to measure viable CFU counts. IC90, IC99 and IC99.9 values are calculated by linear regression analysis.

For the in vitro killing assay with P10 variants, *S. aureus* JAR (1 min CFU/ml) were incubated for 2 hours at 37° C. with various concentrations of the peptides in PBS or in PBS/human plasma (1/1, v/v). Depicted in Tables 2-6 is the concentration of the peptide that resulted in killing of 99.9% of the bacteria (1000 CFU/ml remaining). The LC99.9 is the average value of two independent experiments.

Human Skin Equivalent

Human skin equivalents were prepared as described in El Ghalbzouri et al. (*Lab. Invest.* 2004 January; 84(1):102-12). In brief, 5×10$^5$ normal human keratinocytes were seeded onto fibroblast-populated rat-tail collagen matrices. The collagen matrices were prepared in advance by making a basal (0.1% acetic acid, 4 mg/ml collagen, Hank's Balanced Salt Solution (HBSS, 10×), 1 M NaOH and FCS) and a top collagen layer in which normal human fibroblasts were seeded (4 mg/ml collagen, 10×HBSS, 1 M NaOH, FCS and fibroblasts). Transwell filters with 3 μm pore size (Corning 3414, Costar) were used to culture the human skin equivalents. The collagen matrices were cultured in fibroblast medium for a week. The full thickness human skin equivalents were first cultured submerged in keratinocyte medium for 2 or 3 days at 37° C. and 7.3% CO$_2$ and were then cultured in keratinocyte medium as described above, but with 1% FCS and supplemented with 2 M L-serine, 10 mM L-carnitine, 1 μM DL-α-tocopherol-acetate, 50 μM ascorbic acid, a lipid supplement that contained palmitic acid, linoleic acid and arachidonic acid in a 1:1:1 ratio and 2.4×10$^{-5}$ M bovine serum albumin. After 2 or 3 days, the HSEs were then cultured at the air-liquid interface for 14 days in keratinocyte medium as described above, but without serum and supplemented with 2 M L-serine, 10 mM L-carnitine, 1 μM DL-α-tocopherol-acetate, 50 μM ascorbic acid, a lipid supplement that contained 25 μM palmitic acid, 30 μM linoleic acid and 7 μM arachidonic acid (2:1:1) and 2.4×10$^{-5}$ M bovine serum albumin. Culture medium was refreshed twice a week.

Burn Wound Infection Model and Experimental Treatment

Full-thickness skin models were reconstructed as described above using transwell filters with a pore size of 0.4 μm, Corning 3460, Costar). After 10 days of culturing at the air-liquid interphase, burn wounds of 20 mm$^2$ were made by applying liquid nitrogen on the skin equivalents for 15 seconds. The thermally injured skin equivalents were incubated for 1 hour at 37° C. and 7.3% CO$_2$ before infection. Infection was done by applying an inoculum of 1×10$^5$ MRSA onto the skin equivalents. After incubation for 1 hour, the non-adherent bacteria were removed. Treatment started 1 hour or 8 hours after infection and one dose (100 μg in 100 ml of PBS) of LL-37, P60.4Ac or P10 was given. Treatment was prolonged for 4 hours or 24 hours before processing. The skin equivalents were washed with 1 ml of PBS to remove all non-adherent bacteria. Then two biopsies of 4 mm were taken and homogenized in 1 ml of PBS. The homogenates and the washes were serially diluted to measure viable CFU counts on diagnostic sensitivity test (DST) agar plates.

Results

Identification of P10

A set of 15 peptides was synthesized. The peptides were designed to either strengthen or weaken the predicted amphipathic structure when compared to P60.4Ac (M. J. Nell et al., *Peptides* (2006) 649-660), as based on computer-assisted structure predictions. Anti-biofilm activity is highly variable among the peptides (both higher and lower activity antimicrobial peptides were generated in this way). It was anticipated that a delicate relation exists between modification of the amphipathic helical structure and anti-biofilm activity within antimicrobial peptides. Therefore, a series of short synthetic peptides were developed based on these observations, and their antimicrobial activity was evaluated. The activity of these peptides varied from no antimicrobial activity, to peptides with an activity that exceeded that of LL-37 on a molar basis.

The sequences of P60.4Ac and the 15 peptides tested are:

```
P60.4Ac
                                    (SEQ ID NO: 41)
IGKEFKRIVERIKRFLRELVRPLR

P2
                                    (SEQ ID NO: 42)
IAKEFKRIVERIKRFLRELVRPLR

P3
                                    (SEQ ID NO: 43)
LARDYKRLVERLKRWLRELVRPLK

P4
                                    (SEQ ID NO: 44)
IAKEFKRILERIKRFIREITRPIR

P5
                                    (SEQ ID NO: 45)
TAKEYKRILDRIKRYLRELVRAIK

P6
                                    (SEQ ID NO: 46)
VAKDYRKVVDRIKRFLRYLLRPVR

P9
                                    (SEQ ID NO: 47)
LAKDYKKIVERLRKWLREVLRPVK

P10
                                    (SEQ ID NO: 48)
LAREYKKIVEKLKRWLRQVLRTLR

P11
                                    (SEQ ID NO: 49)
LAKEYRKIFDRLKKWLRQIVRPSK

P12
                                    (SEQ ID NO: 50)
LAREYKRIFERLRKWLRQIVKPVR

P13
                                    (SEQ ID NO: 51)
LAKEWRKIVDRLKRWLRDILKATK

P14
                                    (SEQ ID NO: 52)
VAREWKRILEKIKRWLRDILKALR

P15
                                    (SEQ ID NO: 53)
VAKEWRKIVDRIKRYLRDISKATK

P16
                                    (SEQ ID NO: 54)
TAREWKRILEKIRKYLRDVSRVIR

P17
                                    (SEQ ID NO: 55)
VAKDWKRIVDKVRRYLREVTKILK

P19
                                    (SEQ ID NO: 56)
TAKDYRKIFEKIKKYLKDLTRILK
```

Figure 2A:
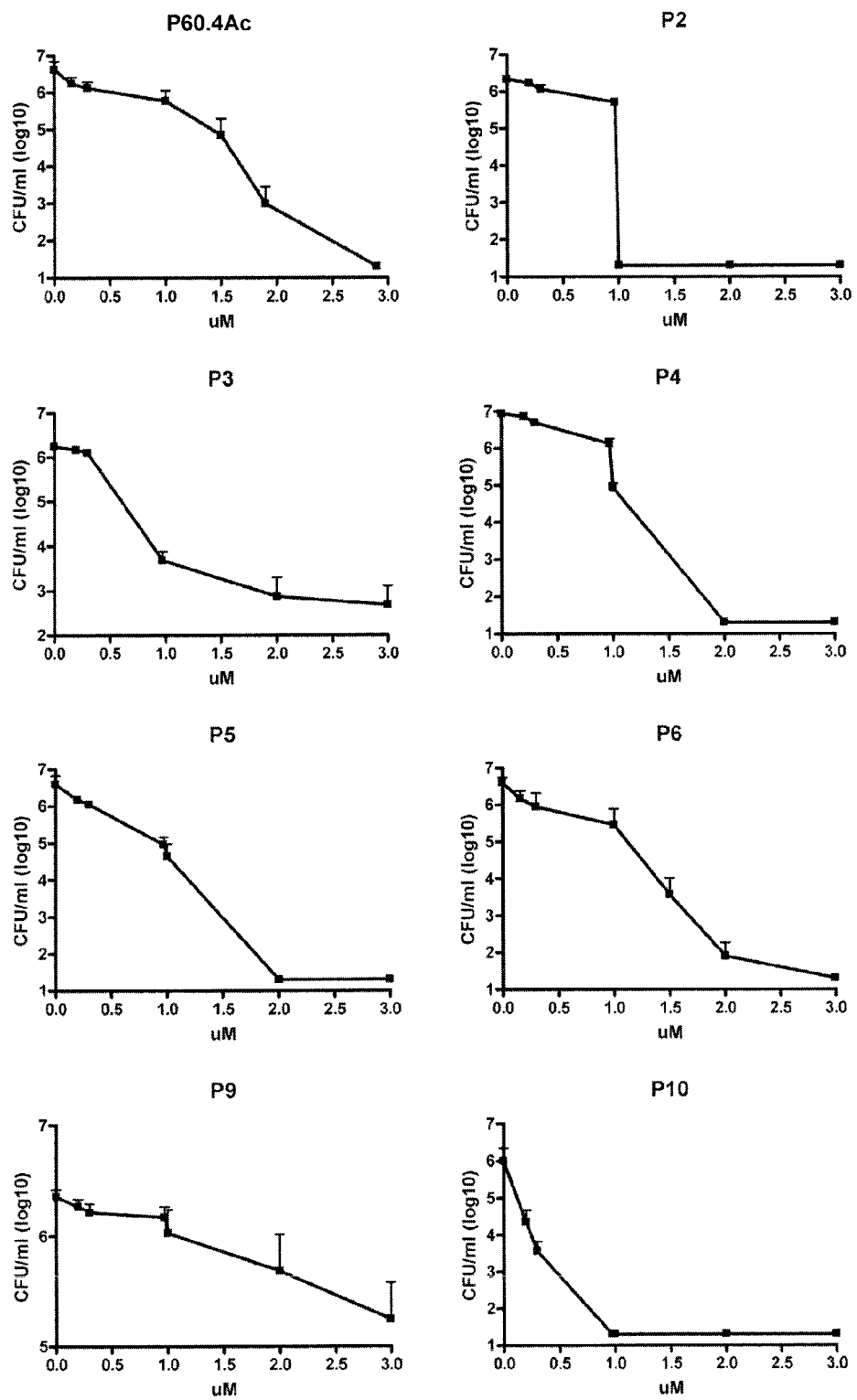
Figure 2A:
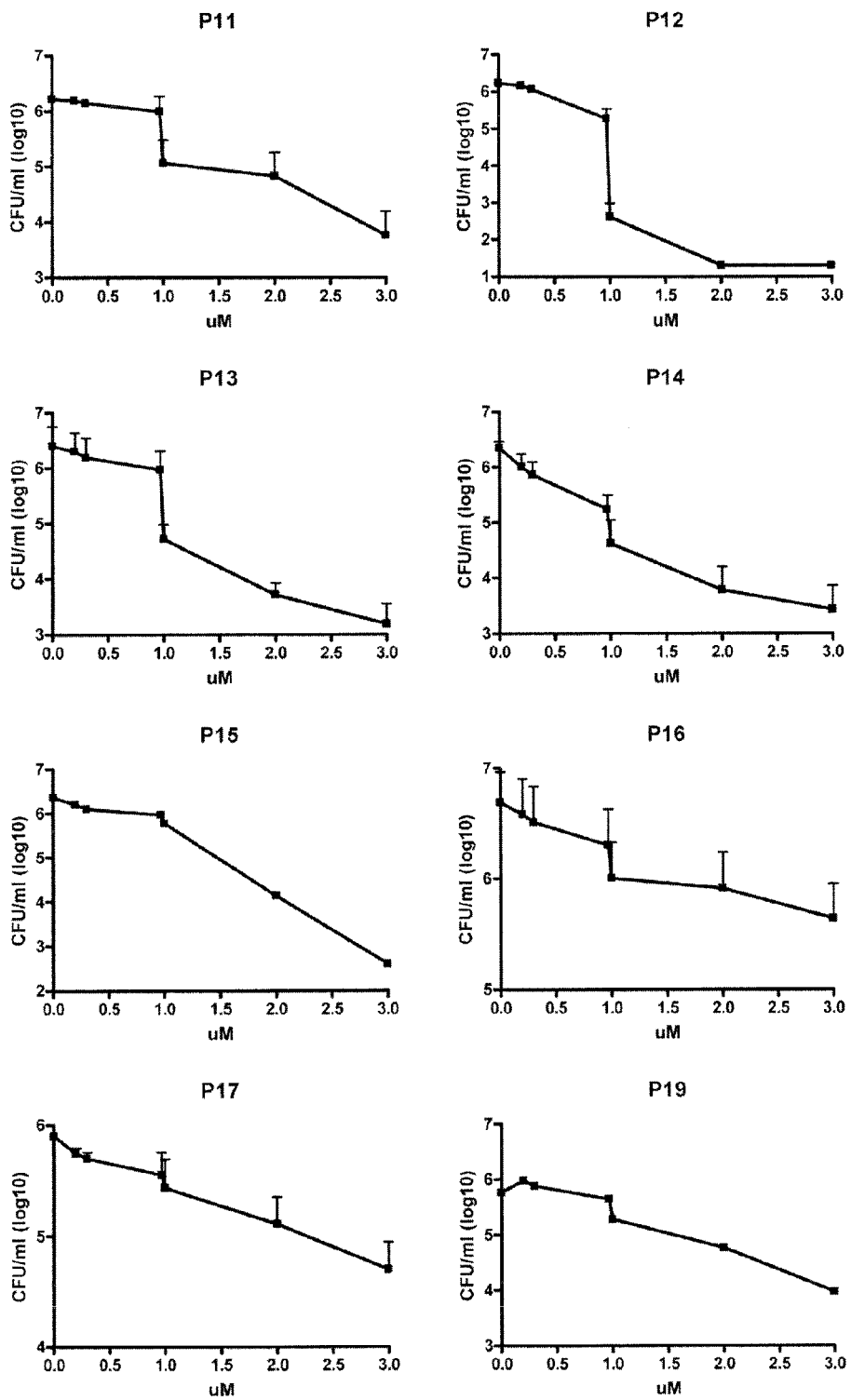

Peptide P10 kills MRSA LYH14616 very efficiently. It has the highest activity against MRSA LUH14616 of all peptides tested, and is even considerably more effective than P60.4Ac (OP-145), see FIGS. 2A and 2B. For instance, P10 has an IC99.9 of 0.59 µM, meaning that at this concentration, P10 kills 999 out of 1000 bacteria. P60.4Ac, at a similar, even slightly higher concentration of 0.75 µM, kills only 900 out of 1000 bacteria (IC90 of 0.75 µM). Thus, 100 times more bacteria survive after treatment with P60.4Ac as compared to treatment with P10 at a similar concentration. Hence, P10 has an approximately 100 times better activity than P60.4Ac.

Activity of P10 and Variants

Figure 3:
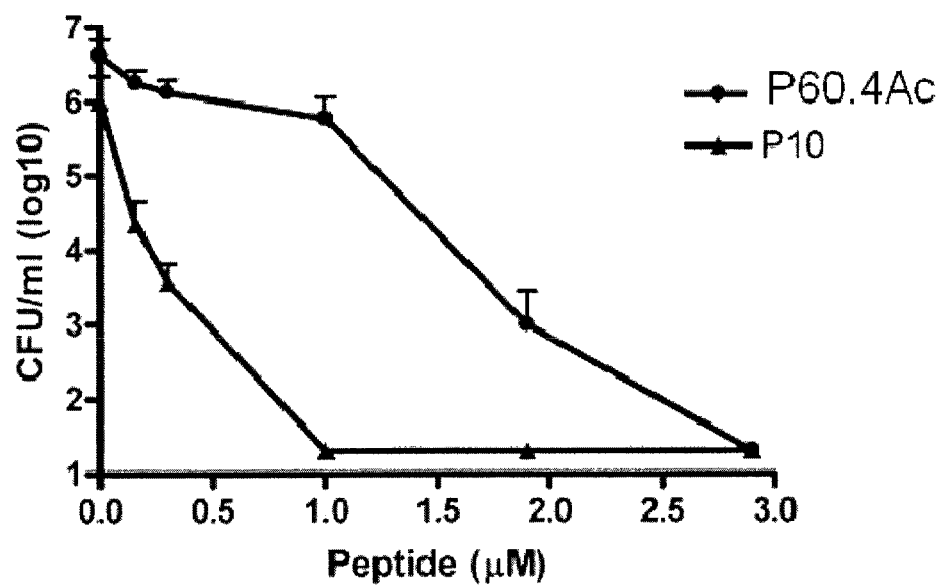
FIG. 3: Killing of MRSA by different concentrations of P60.4Ac and P10, as shown by the amount of CFU of MRSA per ml of culture medium.
Figure 4:
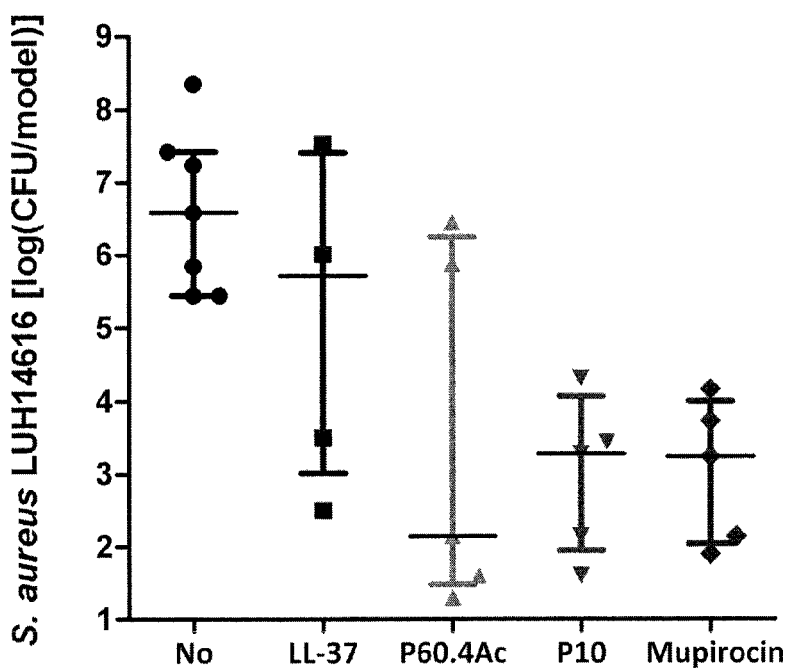
FIG. 4: Effect of LL-37, P60.4Ac, P10 and mupirocin on MRSA LUH14616 in thermally wounded skin model depicted as the amount of CFU of MRSA LUH14616 per skin model (Panel A) and survival of MRSA LUH14616 (in %) per skin model (Panel B).
Figure 4:
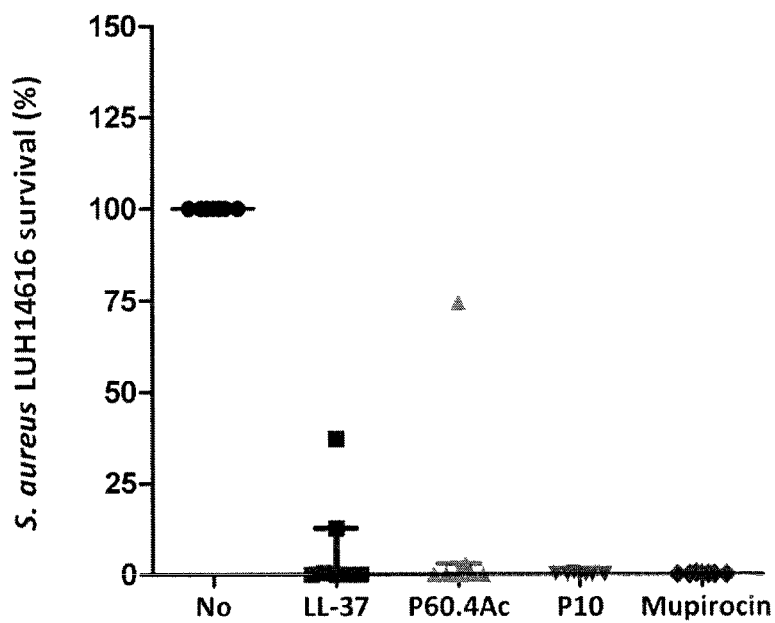
Figure 5:
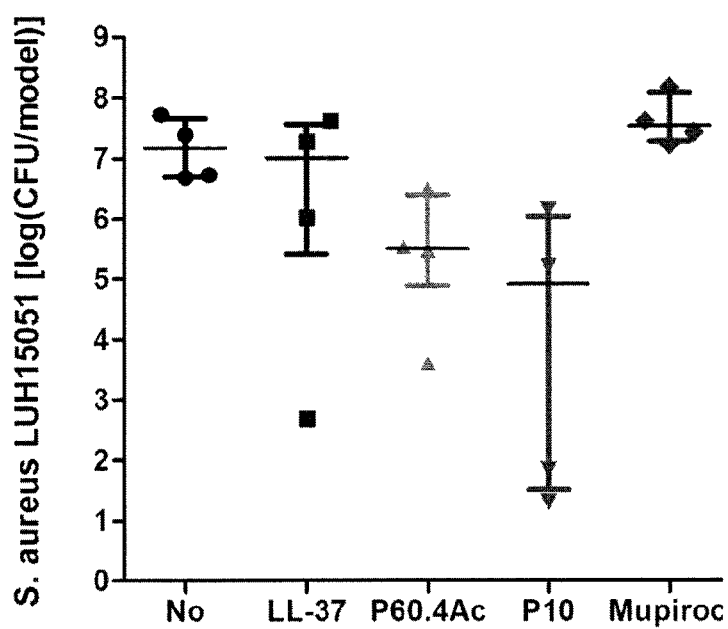
FIG. 5: Effect of LL-37, P60.4AC, P10 and mupirocin on mupirocin-resistant MRSA LUH15051 in thermally wounded skin model depicted as the amount of CFU of MRSA LUH15051 per skin model (Panel A) and survival of MRSA LUH15051 (in %) per skin model (Panel B).
Figure 5:
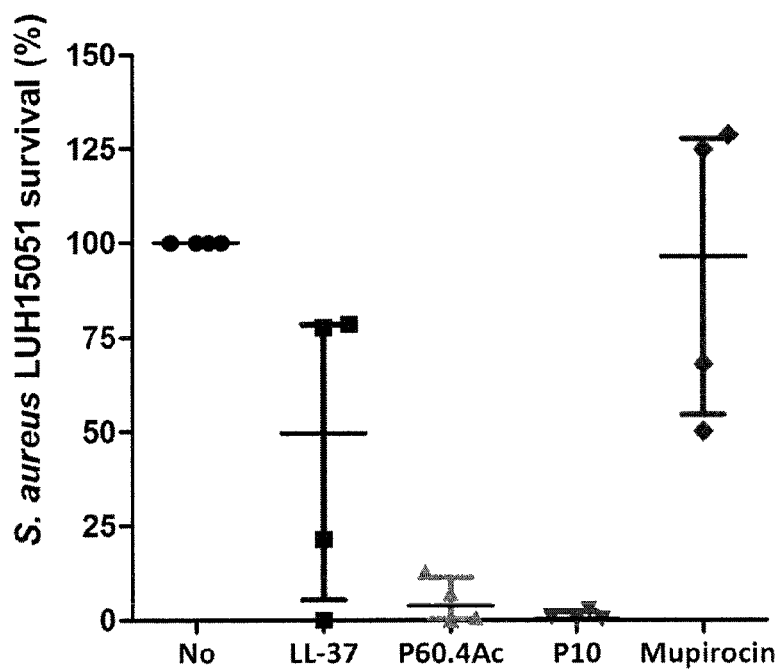

Peptide 10 was more effective than LL-37 and P60.4Ac in killing MRSA and mupirocine-resistant MRSA and in eliminating these bacteria from thermally wounded human skin equivalents (FIGS. 3-5).

P10 is highly effective against MRSA bacteria in log phase, stationary bacteria and bacteria residing in biofilms.

In addition, P10 is highly effective against:

1) Gram-positive bacteria, e.g., various strains of methicilline-resistant as well as -sensitive strains (see FIGS. 4 and 5), *Staphylococcus epidermidis*, 2) Gram-negative bacteria including various (drug-resistant) *Pseudomonas aeruginosa* strains, (drug-resistant) *Acinetobacter baumannii* strains, 3) mycobacteria, and 4) the fungal pathogens (fluconazole-resistant) *Candida albicans* and *Aspergillus niger*.

P10 variants in which one or all amino acids have been replaced by their corresponding D-amino acid, or one amino acid has been replaced by another L-amino acid have antimicrobial activity that is comparable to that of P10. Also, variants having an elongated N-terminal or C-terminal with different groups including acetyl, amide, NH—($CH_2$—$CH_2$—O)$_{11}$—CO, hexanoyl, decanoyl, myristoyl, propionyl, one or two amino-hexanoyl groups, and shorter P-10 variants have antimicrobial activity that is comparable to that of P10. The sequence and activity of these P10 variants are shown in Tables 2, 3, 5 and 6. Peptides in which proline substitutions were introduced to break the helix were mostly inactive (see Table 4).

TABLE 2

Activity of P-10 variants in which one amino acid has been replaced by its D-amino acid (lower case letters) and counterpart and retro-inverso peptide. J = acetyl, B = amide

| Peptide | Sequence | LC99.9 (µM) (PBS) | LC99.9 (µM) (50% plasma) | SEQ ID NO: |
|---|---|---|---|---|
| P-10 | JLAREYKKIVEKLKRWLRQVLRTLRB | 1.6 | 102.4 | 110 |
| 1301-1 | JlAREYKKIVEKLKRWLRQVLRTLRB | 0.6 | 38.4 | 110 |
| 1301-2 | JLaREYKKIVEKLKRWLRQVLRTLRB | 0.6 | 38.4 | 110 |
| 1301-3 | JLArEYKKIVEKLKRWLRQVLRTLRB | 0.6 | 38.4 | 110 |
| 1301-4 | JLAReYKKIVEKLKRWLRQVLRTLRB | 0.6 | 38.4 | 110 |
| 1301-5 | JLAREyKKIVEKLKRWLRQVLRTLRB | 0.6 | 38.4 | 110 |
| 1301-6 | JLAREYkKIVEKLKRWLRQVLRTLRB | 0.6 | 38.4 | 110 |
| 1301-7 | JLAREYKkIVEKLKRWLRQVLRTLRB | 0.6 | 25.6 | 110 |
| 1301-8 | JLAREYKKiVEKLKRWLRQVLRTLRB | 0.6 | 38.4 | 110 |
| 1301-9 | JLAREYKKIvEKLKRWLRQVLRTLRB | 0.6 | 38.4 | 110 |
| 1301-10 | JLAREYKKIVeKLKRWLRQVLRTLRB | 0.6 | 38.4 | 110 |
| 1301-11 | JLAREYKKIVEkLKRWLRQVLRTLRB | 0.4 | 19.2 | 110 |
| 1301-12 | JLAREYKKIVEKlKRWLRQVLRTLRB | 0.6 | 32.0 | 110 |
| 1301-13 | JLAREYKKIVEKLkRWLRQVLRTLRB | 0.6 | 38.4 | 110 |
| 1301-14 | JLAREYKKIVEKLKrWLRQVLRTLRB | 0.6 | 38.4 | 110 |
| 1301-15 | JLAREYKKIVEKLKRwLRQVLRTLRB | 0.4 | 38.4 | 110 |
| 1301-16 | JLAREYKKIVEKLKRWlRQVLRTLRB | 0.6 | 38.4 | 110 |
| 1301-17 | JLAREYKKIVEKLKRWLrQVLRTLRB | 0.6 | 38.4 | 110 |
| 1301-18 | JLAREYKKIVEKLKRWLRqVLRTLRB | 0.6 | 38.4 | 110 |
| 1301-19 | JLAREYKKIVEKLKRWLRQvLRTLRB | 0.6 | 32.0 | 110 |
| 1301-20 | JLAREYKKIVEKLKRWLRQVlRTLRB | 0.6 | 38.4 | 110 |
| 1301-21 | JLAREYKKIVEKLKRWLRQVLrTLRB | 0.6 | 38.4 | 110 |
| 1301-22 | JLAREYKKIVEKLKRWLRQVLRtLRB | 0.6 | 38.4 | 110 |
| 1301-23 | JLAREYKKIVEKLKRWLRQVLRTlRB | 0.4 | 32.0 | 110 |
| 1301-24 | JLAREYKKIVEKLKRWLRQVLRTLrB | 0.6 | 19.2 | 110 |
| 1241-03 | rltrlvqrlwrklkevikkyeralB | 3.2 | >102.4 | |
| 1313-07 | JlareykkiveklkrwlrqvlrtlrB | 1.6 | 25.6 | |

TABLE 3

Activity of P-10 variants in which the peptide has been elongated N-terminally or C-terminally with different groups. J = acetyl, B = amide, o = NH-(CH$_2$-CH$_2$-O)$_{11}$-CO, b = hexanoyl, j = decanoyl, u = myristoyl, U = propionyl. Z = amino-hexanoyl

| Peptide | Sequence | LC99.9 (µM) (PBS) | LC99.9 (µM) (50% plasma) | SEQ ID NO: |
|---|---|---|---|---|
| P-10 | JLAREYKKIVEKLKRWLRQVLRTLRB | 1.6 | 102.4 | 112 |
| 1302-4 | JLAREYKKIVEKLKRWLRQVLRTLRZZB | 0.8 | 38.4 | 112 |

TABLE 3-continued

Activity of P-10 variants in which the peptide has been elongated N-terminally or C-terminally with different groups. J = acetyl, B = amide, o = NH-(CH$_2$-CH$_2$-O)$_{11}$-CO, b = hexanoyl, j = decanoyl, u = myristoyl, U = propionyl. Z = amino-hexanoyl

| Peptide | Sequence | LC99.9 (μM) (PBS) | LC99.9 (μM) (50% plasma) | SEQ ID NO: |
| --- | --- | --- | --- | --- |
| 1302-5 | JLAREYKKIVEKLKRWLRQVLRTLRoB | 0.8 | 102.4 | 112 |
| 1302-6 | JLAREYKKIVEKLKRWLRQVLRTLRZB | 0.6 | 38.4 | 112 |
| 1302-7 | oLAREYKKIVEKLKRWLRQVLRTLRB | 1.6 | 102.4 | 112 |
| 1302-8 | bLAREYKKIVEKLKRWLRQVLRTLRB | 1.2 | 102.4 | 112 |
| 1302-9 | jLAREYKKIVEKLKRWLRQVLRTLRB | 1.6 | >102.4 | 112 |
| 1302-10 | uLAREYKKIVEKLKRWLRQVLRTLRB | 2.0 | 102.4 | 112 |
| 1302-11 | ULAREYKKIVEKLKRWLRQVLRTLRB | 1.6 | 102.4 | 112 |

TABLE 4

Activity of P-10 variants in which the peptide has been modified by two substitutions of a particular amino acid by P (proline, which has been reported to be a helix breaking residue). J = acetyl, B = amide

| Peptide | Sequence | LC99.9 (μM) (PBS) | LC99.9 (μM) (50% plasma) | SEQ ID NO: |
| --- | --- | --- | --- | --- |
| P-10 | JLAREYKKIVEKLKRWLRQVLRTLRB | 1.6 | 102.4 | 111 |
| 1302-13 | JLAREYKPIVEKLKRWPRQVLRTLRB | >3.2 | >102.4 | 111 |
| 1302-14 | JLAREYPKIVEKLKRWLRPVLRTLRB | 3.2 | 102.4 | 111 |
| 1302-15 | JLAREYKKIVPKLKRWLRQVPRTLRB | >3.2 | 76.8 | 111 |
| 1302-16 | JLAREYKKPVEKLKRWLPQVLRTLRB | >3.2 | 102.4 | 111 |

TABLE 5

Activity of P-10 variants in which one amino acid has been replaced by another L-amino acid. J = acetyl, B = amide

| Peptide | Sequence | LC99.9 (μM) (PBS) | LC99.9 (μM) (50% plasma) | SEQ ID NO: |
| --- | --- | --- | --- | --- |
| P-10 | JLAREYKKIVEKLKRWLRQVLRTLRB | 1.6 | 102.4 | 109 |
| 1302-17 | JIAREYKKIVEKLKRWLRQVLRTLRB | 1.6 | 102.4 | 109 |
| 1302-18 | JVAREYKKIVEKLKRWLRQVLRTLRB | 1.6 | 76.8 | 109 |
| 1302-19 | JAAREYKKIVEKLKRWLRQVLRTLRB | 1.6 | 76.8 | 109 |
| 1302-20 | JLLREYKKIVEKLKRWLRQVLRTLRB | 1.6 | 102.4 | 109 |
| 1302-21 | JLVREYKKIVEKLKRWLRQVLRTLRB | 1.2 | 76.8 | 109 |
| 1302-22 | JLQREYKKIVEKLKRWLRQVLRTLRB | 1.6 | 76.8 | 109 |
| 1302-23 | JLAKEYKKIVEKLKRWLRQVLRTLRB | 1.6 | 102.4 | 109 |
| 1302-24 | JLAHEYKKIVEKLKRWLRQVLRTLRB | 1.6 | 102.4 | 109 |
| 1302-25 | JLARQYKKIVEKLKRWLRQVLRTLRB | 1.2 | 51.2 | 109 |

TABLE 5-continued

Activity of P-10 variants in which one amino acid has been replaced by another L-amino acid. J = acetyl, B = amide

| Peptide | Sequence | LC99.9 (μM) (PBS) | LC99.9 (μM) (50% plasma) | SEQ ID NO: |
|---|---|---|---|---|
| 1302-26 | JLARPFKKIVFKTKRWLRQVIRTTRR | 0.8 | 76.8 | 109 |
| 1302-27 | JLAREYRKIVEKLKRWLRQVLRTLRB | 0.8 | 76.8 | 109 |
| 1302-28 | JLAREYHKIVEKLKRWLRQVLRTLRB | 1.2 | 102.4 | 109 |
| 1302-29 | JLAREYKRIVEKLKRWLRQVLRTLRB | 1.6 | 102.4 | 109 |
| 1302-30 | JLAREYKHIVEKLKRWLRQVLRTLRB | 3.2 | 102.4 | 109 |
| 1302-31 | JLAREYKKIVERLKRWLRQVLRTLRB | 3.2 | 102.4 | 109 |
| 1302-32 | JLAREYKKIVERLKRWLRQVLRTLRB | 3.2 | 102.4 | 109 |
| 1302-33 | JLAREYKKIVEKIKRWLRQVLRTLRB | 3.2 | 102.4 | 109 |
| 1302-34 | JLAREYKKIVEKVKRWLRQVLRTLRB | 3.2 | 102.4 | 109 |
| 1302-36 | JLAREYKKIVEKAKRWLRQVLRTLRB | 3.2 | 76.8 | 109 |
| 1302-37 | JLAREYKKIVEKLHRWLRQVLRTLRB | 3.2 | 102.4 | 109 |
| 1302-38 | JLAREYKKIVEKLKKWLRQVLRTLRB | 2.4 | 102.4 | 109 |
| 1302-39 | JLAREYKKIVEKLKHWLRQVLRTLRB | 3.2 | 102.4 | 109 |
| 1302-40 | JLAREYKKIVEKLKRFLRQVLRTLRB | 1.6 | 76.8 | 109 |
| 1302-41 | JLAREYKKIVEKLKRWLHQVLRTLRB | 1.6 | 102.4 | 109 |
| 1302-42 | JLAREYKKIVEKLKRWLRNVLRTLRB | 1.6 | 76.8 | 109 |
| 1302-43 | JLAREYKKIVEKLKRWLRAVLRTLRB | 1.6 | 102.4 | 109 |
| 1302-44 | JLAREYKKIVEKLKRWLRSVLRTLRB | 1.6 | 76.8 | 109 |
| 1302-45 | JLAREYKKIVEKLKRWLRTVLRTLRB | 1.6 | 76.8 | 109 |
| 1302-46 | JLAREYKKIVEKLKRWLRQLLRTLRB | 1.6 | 102.4 | 109 |
| 1302-47 | JLAREYKKIVEKLKRWLRQVIRTLRB | 1.6 | 76.8 | 109 |
| 1302-48 | JLAREYKKIVEKLKRWLRQVVRTLRB | 1.2 | 76.8 | 109 |
| 1302-49 | JLAREYKKIVEKLKRWLRQVARTLRB | 1.6 | 51.2 | 109 |
| 1302-50 | JLAREYKKIVEKLKRWLRQVLKTLRB | 0.8 | 51.2 | 109 |
| 1302-51 | JLAREYKKIVEKLKRWLRQVLHTLRB | 1.6 | 102.4 | 109 |
| 1302-52 | JLAREYKKIVEKLKRWLRQVLRQLRB | 1.6 | 76.8 | 109 |
| 1302-53 | JLAREYKKIVEKLKRWLRQVLRNLRB | 1.6 | 51.2 | 109 |
| 1302-54 | JLAREYKKIVEKLKRWLRQVLRALRB | 0.8 | 51.2 | 109 |
| 1302-55 | JLAREYKKIVEKLKRWLRQVLRTLHB | 1.2 | 102.4 | 109 |

TABLE 6

Activity of shorter P-10 variants. J = acetyl, B = amide

| Peptide | Sequence | LC99.9 (μM) (PBS) | LC99.9 (μM) (50% plasma) | SEQ ID NO: |
|---|---|---|---|---|
| P-10 | JLAREYKKIVEKLKRWLRQVLRTLRB | 1.6 | 102.4 | 113 |
| 1302-56 | JREYKKIVEKLKRWLRQVLRTLRB | 1.6 | 51.2 | 113 |

TABLE 6-continued

Activity of shorter P-10 variants. J = acetyl, B = amide

| Peptide | Sequence | LC99.9 (µM) (PBS) | LC99.9 (µM) (50% plasma) | SEQ ID NO: |
|---|---|---|---|---|
| 1302-57 | JLAREYKKIVEKLKRWLRQVLRTB | 1.6 | 51.2 | 113 |
| 1302-58 | JREYKKIVEKLKRWLRQVLRTB | 1.6 | 76.8 | 113 |
| 1302-59 | JYKKIVEKLKRWLRQVLRTLRB | 1.6 | 51.2 | 113 |
| 1302-60 | JLAREYKKIVEKLKRWLRQVLB | 1.6 | 102.4 | 113 |
| 1302-61 | JEYKKIVEKLKRWLRQVLRB | 2.4 | 102.4 | 113 |
| 1302-62 | JYKKIVEKLKRWLRQVLB | 1.6 | 76.8 | 113 |
| 1302-63 | JKKIVEKLKRWLRQB | >3.2 | 102.4 | 113 |

The invention claimed is:

1. A polypeptide comprising LAREYKKIVEKLKRWL-RQVLRTLR (SEQ ID NO:1), or a variant thereof,
said polypeptide having antimicrobial, antibacterial, antiviral, antifungal, antiparasitic and/or anti-inflammatory activity,
said variant having at least 16 amino acids and:
having up to 5 of the following amino acid substitutions:
substitution of one or more amino acids selected from the group consisting of L, I, V or A by another amino acid selected from said group;
substitution of one or more amino acids selected from the group consisting of R, K or H by another amino acid selected from said group;
substitution of E by Q;
substitution of Y or W by F; and
substitution of one or more amino acids selected from the group consisting of Q, N, A, S or T by another amino acid selected from said group;
having one or more substitutions of an amino acid by a corresponding D-amino acid,
having one or more substitutions of an amino acid by a corresponding non-natural amino acid, and/or
having a retro-inverso sequence of at least 16 consecutive amino acids from said amino acid sequence.

2. The polypeptide of claim 1, wherein said polypeptide is N-terminally and/or C-terminally modified.

3. The polypeptide of claim 1, wherein said variant comprises at least YKKIVEKLKRWLRQVL (SEQ ID NO:2) having up to 5 of the following amino acid substitutions:
substitution of one or more amino acids selected from the group consisting of L, I, V, or A by another amino acid selected from the group;
substitution of one or more amino acids selected from the group consisting of R, K, or H by another amino acid selected from the group;
substitution of E by Q;
substitution of Y or W by F; and
substitution of one or more amino acids selected from the group consisting of Q, N, A, S, or T by another amino acid selected from said group.

4. The polypeptide of claim 2, wherein the polypeptide is N-terminally and/or C-terminally modified via an N-terminal acetyl-, hexanoyl-, decanoyl-, myristoyl-, NH—($CH_2$—$CH_2$—O)$_{11}$—CO— or propionyl-residue.

5. The polypeptide of claim 2, wherein the polypeptide comprises a C-terminal amide-, NH—($CH_2$—$CH_2$—O)$_{11}$—CO-amide-, or one or two amino-hexanoyl groups.

6. A pharmaceutical composition comprising:
the polypeptide of claim 1; and
at least one pharmaceutically acceptable carrier, diluent and/or excipient.

7. The pharmaceutical composition according to claim 6, which is formulated for topical administration.

8. The pharmaceutical composition of claim 6, further comprising:
an antimicrobial agent.

9. The pharmaceutical composition of claim 6, which comprises a controlled release and/or targeted delivery carrier.

10. The pharmaceutical composition of claim 7, which is a crème, gel, ointment, lotion, foam, suspension, spray, aerosol, or powder aerosol.

11. The pharmaceutical composition of claim 9, wherein the antimicrobial agent is selected from the group consisting of penicillins, cephamosporins, mupirocin, and carbapenems.

12. A coating for a medical device, the coating comprising the polypeptide of claim 1.

13. A method of inhibiting a bacterial microbe, the method comprising: contacting the bacterial microbe with the polypeptide of claim 1.

* * * * *